United States Patent
Yamada et al.

(10) Patent No.: US 12,201,260 B2
(45) Date of Patent: Jan. 21, 2025

(54) CONTROL APPARATUS, DIAGNOSIS SUPPORT METHOD, AND RECORDING MEDIUM

(71) Applicant: OLYMPUS CORPORATION, Tokyo (JP)

(72) Inventors: Tatsuki Yamada, Hachioji (JP); Akihiro Kubota, Kokubunji (JP); Yamato Kanda, Hino (JP); Mitsutaka Kimura, Hino (JP); Makoto Kitamura, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 615 days.

(21) Appl. No.: 17/476,604

(22) Filed: Sep. 16, 2021

(65) Prior Publication Data
US 2022/0000351 A1 Jan. 6, 2022

Related U.S. Application Data

(63) Continuation of application No. PCT/JP2019/011102, filed on Mar. 18, 2019.

(51) Int. Cl.
*A61B 1/00* (2006.01)
*A61B 1/045* (2006.01)
(Continued)

(52) U.S. Cl.
CPC .... *A61B 1/000094* (2022.02); *A61B 1/00045* (2013.01); *A61B 1/045* (2013.01);
(Continued)

(58) Field of Classification Search
CPC ............ A61B 1/000094; A61B 1/0655; A61B 1/00045; A61B 1/045; A61B 1/0684; G16H 50/30; G16H 50/70; G16H 50/20
See application file for complete search history.

(56) References Cited

U.S. PATENT DOCUMENTS

2012/0101372 A1  4/2012  Teramura et al.
2012/0190922 A1* 7/2012  Kaku .................. A61B 1/0005
                                                       600/109
(Continued)

FOREIGN PATENT DOCUMENTS

EP    2 443 992 A2   4/2012
JP    2002-165757 A  6/2002
(Continued)

OTHER PUBLICATIONS

International Search Report dated Jun. 181, 2019 received in PCT/JP2019/011102.
(Continued)

*Primary Examiner* — Khai M Nguyen
(74) *Attorney, Agent, or Firm* — Scully, Scott, Murphy & Presser, P.C.

(57) ABSTRACT

A diagnosis support apparatus includes a processor including at least one piece of hardware. The processor identifies, based on physical information including one or more kinds of information capable of estimating a state of a diagnosis target organ of a subject, one abnormal symptom appearing in the diagnosis target organ, performs, as lesion extraction processing for extracting a lesion candidate region from an endoscopic image, different processing specialized for each abnormal symptom that appears in the diagnosis target organ, and performs the lesion extraction processing corresponding to the identified one abnormal symptom.

20 Claims, 10 Drawing Sheets

(51) Int. Cl.
    *A61B 1/06*     (2006.01)
    *G16H 50/20*     (2018.01)
    *G16H 50/30*     (2018.01)
    *G16H 50/70*     (2018.01)

(52) U.S. Cl.
    CPC .......... *A61B 1/0655* (2022.02); *A61B 1/0684* (2013.01); *G16H 50/20* (2018.01); *G16H 50/30* (2018.01); *G16H 50/70* (2018.01)

(56) References Cited

U.S. PATENT DOCUMENTS

| | | |
|---|---|---|
| 2015/0366444 A1 | 12/2015 | Morimoto et al. |
| 2018/0014902 A1* | 1/2018 | Kitamura ................ A61B 1/045 |
| 2018/0082104 A1 | 3/2018 | Wan et al. |
| 2020/0359884 A1* | 11/2020 | Swisher ................ G02B 27/017 |
| 2021/0321932 A1* | 10/2021 | Borsody ............ A61B 5/02055 |

FOREIGN PATENT DOCUMENTS

| | | |
|---|---|---|
| JP | 2011-212094 A | 10/2011 |
| JP | 2012-152279 A | 8/2012 |
| JP | 2012-157384 A | 8/2012 |
| JP | 2012-249956 A | 12/2012 |
| JP | 5242381 B2 | 7/2013 |
| JP | 2015-181594 A | 10/2015 |
| JP | 2016-007354 A | 1/2016 |
| JP | 2018-517188 A | 6/2018 |
| WO | 2016/140693 A1 | 9/2016 |
| WO | 2016/151711 A1 | 9/2016 |
| WO | 2019/016912 A1 | 1/2019 |
| WO | 2019/039259 A1 | 2/2019 |

OTHER PUBLICATIONS

English abstract only of EP 1 994 878 A1.
International Search Report dated Jun. 18, 2019 received in PCT/JP2019/011102.

* cited by examiner

FIG. 5

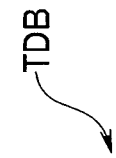

| PHYSICAL INFORMATION | ABNORMAL SYMPTOM | LESION RISK | SPECIAL LIGHT OBSERVATION |
|---|---|---|---|
| HELICOBACTER PYLORI TEST POSITIVE | BACTERIAL INFECTION | 10 | NO |
| HELICOBACTER PYLORI TEST POSITIVE AND PEPSINOGEN TEST NEGATIVE | ULCER | 5 | NO |
| HELICOBACTER PYLORI TEST POSITIVE AND PEPSINOGEN TEST POSITIVE | ATROPHIC GASTRITIS | 20 | NO |
| HELICOBACTER PYLORI TEST NEGATIVE AND PEPSINOGEN TEST POSITIVE | ATROPHIC GASTRITIS | 30 | NO |
| HELICOBACTER PYLORI ELIMINATION TREATMENT COMPLETED | ELIMINATION TREATMENT COMPLETED | 50 | YES |
| CDH1 GENE MUTATION PRESENT | DIFFUSE STOMACH CANCER | 50 | YES |
| EXCISION TREATMENT COMPLETED AND HER2 GENE MUTATION PRESENT | EXCISION TREATMENT COMPLETED | 50 | NO |
| EB VIRUS INFECTION PRESENT | ATROPHIC GASTRITIS | 10 | NO |
| NSAIDs BEING TAKEN | ULCER | 5 | NO |
| SUBJECTIVE SYMPTOM PRESENT | ULCER | 5 | NO |

CONTROL APPARATUS, DIAGNOSIS SUPPORT METHOD, AND RECORDING MEDIUM

CROSS REFERENCE TO RELATED APPLICATION

This application is a continuation application of PCT/JP2019/011102 filed on Mar. 18, 2019, the entire contents of which are incorporated herein by this reference.

BACKGROUND OF THE INVENTION

1. Field of the Invention

The present invention relates to a control apparatus, a diagnosis support method, and a recording medium.

2. Description of the Related Art

In an endoscopic examination in a medical field, as a technique for presenting diagnosis support information, which is information used for a diagnosis of a lesioned part present in an image obtained by picking up an image of an object such as a biological tissue, to a user such as a doctor, there has been known, for example, a technique relating to CAD (computer-aided diagnosis). For example, Japanese Patent Application Laid-Open Publication No. 2011-212094 proposes, for example, a system configured using the technique relating to CAD.

More specifically, Japanese Patent Application Laid-Open Publication No. 2011-212094 discloses a configuration for, in a system including a plurality of lesion extracting units capable of respectively extracting a plurality of lesions of different types, acquiring diagnosis information based on patient information, selecting, out of the plurality of lesion extracting units, one lesion extracting unit corresponding to a discrimination result of presence or absence of a definite diagnosis in the diagnosis information and displaying a lesion extracted by the one lesion extracting unit.

SUMMARY OF THE INVENTION

A control apparatus according to an aspect of the present invention includes a processor including at least one piece of hardware, wherein the processor is configured to: identify, based on physical information including one or more kinds of information capable of estimating a state of a diagnosis target organ of a subject, one abnormal symptom appearing in the diagnosis target organ; perform, as lesion extraction processing for extracting a lesion candidate region from an endoscopic image, different processing specialized for each abnormal symptom that appears in the diagnosis target organ; and perform the lesion extraction processing corresponding to the identified one abnormal symptom.

A diagnosis support method according to an aspect of the present invention includes: identifying, based on physical information including one or more kinds of information capable of estimating a state of a diagnosis target organ of a subject, a symptom appearing in the diagnosis target organ; selecting a different kind of processing for each symptom according to the identified symptom; and performing the selected different kind of processing on an endoscopic image obtained by picking up an image of the diagnosis target organ.

A computer-readable non-transitory recording medium recording a program according to an aspect of the present invention, the program causing a computer to execute: processing for identifying, based on physical information including one or more kinds of information capable of estimating a state of a diagnosis target organ of a subject, a symptom appearing in the diagnosis target organ: processing for selecting a different kind of processing for each symptom according to the identified symptom; and processing for performing the selected different kind of processing on an endoscopic image obtained by picking up an image of the diagnosis target organ.

BRIEF DESCRIPTION OF THE DRAWINGS

FIG. 5 is a diagram showing an example of table data used in processing of a diagnosis support apparatus according to a modification of the first embodiment;

DETAILED DESCRIPTION OF THE PREFERRED EMBODIMENTS

Embodiments of the present invention are explained below with reference to the drawings.

First Embodiment

FIG. 1 to FIG. 6 relate to a first embodiment.

Figure 1:
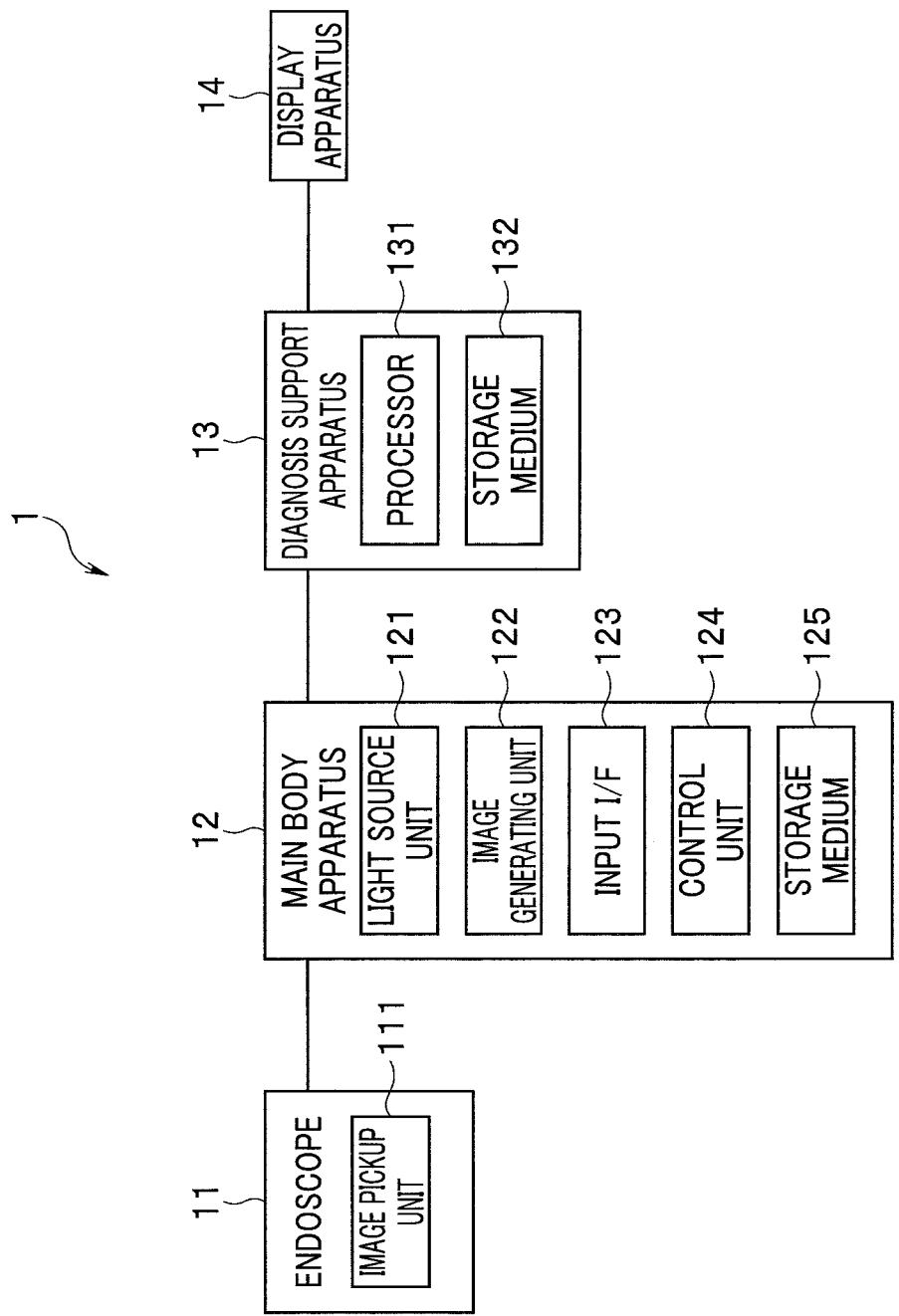
FIG. 1 is a diagram showing a configuration of a main part of an endoscope system including a diagnosis support apparatus according to a first embodiment.

An endoscope system 1 includes, as shown in FIG. 1, an endoscope 11, a main body apparatus 12, a diagnosis support apparatus 13, and a display apparatus 14. FIG. 1 is a diagram showing a configuration of a main part of an endoscope system including a diagnosis support apparatus according to the first embodiment.

The endoscope 11 includes, for example, an elongated-shaped insertion section (not shown) insertable into a subject and an operation section (not shown) provided at a proximal end portion of the insertion section. The endoscope 11 is configured to be removably connected to the main body apparatus 12 via, for example, a universal cable (not shown) extending from the operation section. Inside the endoscope 11, a light guide member (not shown) such as an optical fiber for guiding illumination light supplied from the main body apparatus 12 and emitting the illumination light from a distal end portion of the insertion section is provided. An image pickup unit 111 is provided at the distal end portion of the insertion section of the endoscope 11.

The image pickup unit 111 includes an image pickup device such as a CCD image sensor or a CMOS image sensor. The image pickup unit 111 is configured to pick up an image of return light from an object illuminated by the illumination light emitted through the distal end portion of the insertion section of the endoscope 11, generate an image pickup signal corresponding to the return light, the image of which is picked up, and output the image pickup signal to the main body apparatus 12.

The main body apparatus 12 is configured to be removably connected to each of the endoscope 11 and the diagnosis support apparatus 13. The main body apparatus 12 includes, for example, as shown in FIG. 1, a light source unit 121, an image generating unit 122, an input I/F (interface) 123, a control unit 124, and a storage medium 125.

The light source unit 121 includes one or more light emitting elements such as LEDs. More specifically, the light source unit 121 includes, for example, a blue LED that generates blue light (hereinafter referred to as B light as well), a green LED that generates green light (hereinafter referred to as G light as well), and a red LED that generates red light (hereinafter referred to as R light as well). The light source unit 121 is configured to be able to generate, for example, by limiting wavelength bands of the B light and the G light with optical filters or the like, BN light equivalent to narrow band light having a peak wavelength near 415 nm and GN light equivalent to narrow band light having a peak wavelength near 540 nm. The light source unit 121 is configured to be able to generate illumination light corresponding to control by the control unit 124 and supply the illumination light to the endoscope 11.

The image generating unit 122 is configured to be able to generate an endoscopic image based on an image pickup signal outputted from the endoscope 11 and sequentially output the generated endoscopic image to the diagnosis support apparatus 13 frame by frame.

The input I/F 123 includes one or more switches and/or buttons capable of inputting an instruction, information, and the like corresponding to operation of a user. More specifically, the input I/F 123 is configured to be able to input, for example, physical information including one or more kinds of information capable of estimating a state of a diagnosis target organ of a subject who receives an endoscopic examination. In the input I/F 123, an observation mode changeover switch capable of performing an instruction for setting an observation mode in performing an observation by the endoscope 11 to one of a white light observation mode for observing an object on which the B light, the G light, and the R light are irradiated as illumination light and a special light observation (narrow band light observation) mode for observing an object on which the BN light and the GN light are irradiated as illumination light is provided. In the input I/F 123, an abnormal finding detection instruction switch capable of performing an instruction to perform detection of an abnormal finding from an endoscopic image being currently observed (hereinafter abbreviated as abnormal finding detection instruction) is provided. Note that the observation mode changeover switch and/or the abnormal finding detection instruction switch explained above is not limited to be provided in the input I/F 123 of the main body apparatus 12 and may be provided in, for example, the operation section of the endoscope 11.

The control unit 124 is configured to perform, based on an instruction inputted in the input I/F 123, control relating to operations of the respective units of the endoscope 11 and the main body apparatus 12. The control unit 124 is configured to be able to perform an operation for outputting the instruction inputted in the input i/F 123 to the diagnosis support apparatus 13. The control unit 124 is configured to be able to perform an operation for outputting information such as physical information inputted in the input I/F 123 to the diagnosis support apparatus 13.

In the present embodiment, the image generating unit 122 and the control unit 124 of the main body apparatus 12 may be configured as individual electronic circuits or may be configured as circuit blocks in an integrated circuit such as an FPGA (field programmable gate array). In the present embodiment, the main body apparatus 12 may include one or more processors (CPUs or the like). By modifying a configuration relating to the present embodiment as appropriate, for example, a computer may read, from a storage medium 125 such as a memory, a program for causing the computer to execute functions of the image generating unit 122 and the control unit 124 and perform an operation corresponding to the read program.

Figure 2:
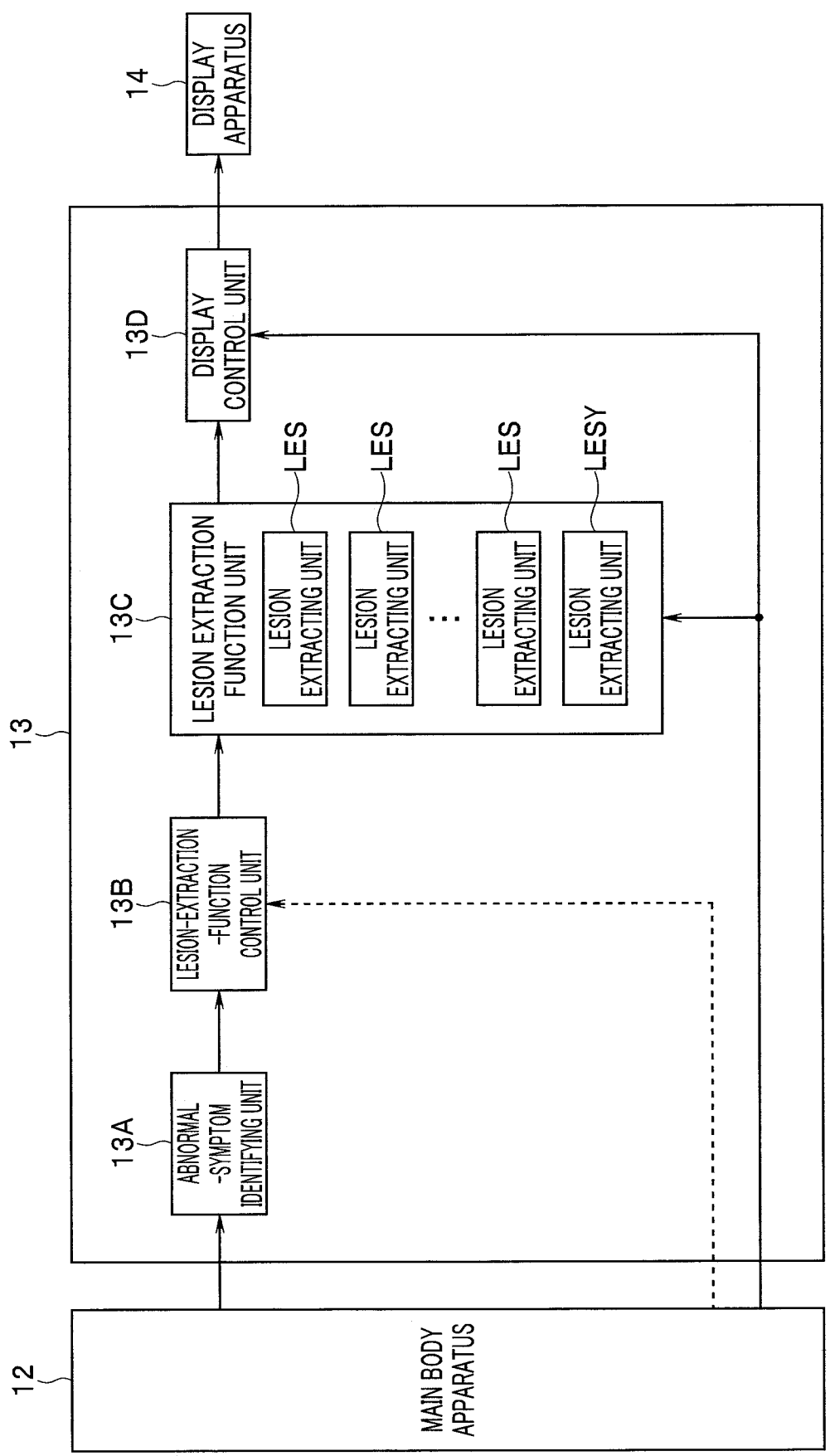
FIG. 2 is a block diagram for explaining a specific example of a configuration of the diagnosis support apparatus according to the first embodiment.

The diagnosis support apparatus 13 is configured as a computer including, for example, one or more processors 131 and a storage medium 132. The diagnosis support apparatus 13 is configured to be removably connected to each of the main body apparatus 12 and the display apparatus 14. The diagnosis support apparatus 13 is configured to perform, based on an instruction and/or information outputted from the main body apparatus 12, lesion extraction processing for extracting a lesion candidate region from an endoscopic image outputted from the main body apparatus 12. Note that it is assumed that the lesion candidate region explained above is extracted as a region including an abnormal finding such as a benign tumor or a malignant tumor. The diagnosis support apparatus 13 is configured to generate a display image by adding visual information indicating a position of the lesion candidate region extracted by the lesion extraction processing explained above to the endoscopic image and output the generated display image to the display apparatus 14. The diagnosis support apparatus 13 includes, for example, as shown in FIG. 2, an abnormal-symptom identifying unit 13A, a lesion-extraction-function control unit 13B, a lesion extraction function unit 13C, and a display control unit 13D. FIG. 2 is a block diagram for explaining a specific example of a configuration of the diagnosis support apparatus according to the first embodiment.

The abnormal-symptom identifying unit 13A is configured to perform, based on physical information outputted from the main body apparatus 12, processing for identifying one abnormal symptom appearing in a diagnosis target organ of a subject who receives an endoscopic examination. The abnormal-symptom identifying unit 13A is configured to output information indicating the one abnormal symptom identified by the processing explained above to the lesion-extraction-function control unit 13B.

The lesion-extraction-function control unit 13B is configured to perform, based on the information outputted from the abnormal-symptom identifying unit 13A, processing for selecting one lesion extracting unit corresponding to the one abnormal symptom included in the information out of a plurality of lesion extracting units included in the lesion extraction function unit 13C. The lesion-extraction-function control unit 13B is configured to perform control for causing the one lesion extracting unit selected by the processing explained above to perform the lesion extraction processing.

The lesion extraction function unit 13C includes a plurality of lesion extracting units LES and a lesion extracting unit LESY.

The plurality of lesion extracting units LES are configured to perform, as the lesion extraction processing for extracting a lesion candidate region from an endoscopic image obtained by picking up an image of a diagnosis target organ of a subject who receives an endoscopic examination, different processing specialized for each abnormal symptom that could appear in the diagnosis target organ.

The lesion extracting unit LESY is configured to perform, as the lesion extraction processing for extracting a lesion candidate region from an endoscopic image obtained by picking up an image of a diagnosis target organ of a subject who receives an endoscopic examination, processing not specialized for a specific abnormal symptom that could appear in the diagnosis target organ.

The lesion extraction function unit 13C is configured to perform, according to control by the lesion-extraction-function control unit 13B, in a lesion extracting unit LESX selected out of the plurality of lesion extracting units LES or the lesion extracting unit LESY selected instead of the lesion extracting unit LESX, lesion extraction processing equivalent to processing for extracting a lesion candidate region from an endoscopic image outputted from the main body apparatus 12. The lesion extraction function unit 13C is configured to output, to the display control unit 13D, information capable of estimating a position of the lesion candidate region extracted by the lesion extraction processing of the lesion extracting unit LESX or the lesion extracting unit LESY to be identified.

The display control unit 13D performs, based on the information outputted from the lesion extraction function unit 13C, processing for identifying a position of a lesion candidate region in an endoscopic image outputted from the main body apparatus 12 and generating visual information indicating the identified position of the lesion candidate region. The display control unit 13D is configured to perform processing for generating a display image by adding the visual information explained above to the endoscopic image and outputting the generated display image to the display apparatus 14.

In the present embodiment, at least a part of functions of the diagnosis support apparatus 13 only has to be realized by the processor 131. In the present embodiment, at least a part of the diagnosis support apparatus 13 may be configured as individual electronic circuits or may be configured as circuit blocks in an integrated circuit such as an FPGA (field programmable gate array). By modifying the configuration according to the present embodiment as appropriate, for example, a computer may read, from the storage medium 132 such as a memory, a program for causing the diagnosis support apparatus 13 to execute at least a part of the functions of the diagnosis support apparatus 13 and perform an operation corresponding to the read program.

The display apparatus 14 is configured to be removably connected to the diagnosis support apparatus 13. The display apparatus 14 includes a monitor and is configured to be able to display a display image outputted from the diagnosis support apparatus 13.

Subsequently, action in the present embodiment is explained. Note that, in the following explanation, a case in which a diagnosis target organ of a subject who receives an endoscopic examination is a stomach is explained as an example. In the following explanation, it is assumed that the observation mode in performing an observation by the endoscope 11 is set in advance to the white color observation mode.

After connecting the respective units of the endoscope system 1 and turning on the endoscope system 1, a user such as a surgeon operates the input I/F 123 to thereby input, as physical information of the subject who receives the endoscopic examination, one or more kinds of information capable of estimating a state of the stomach of the subject.

More specifically, the user inputs, as the physical information of the subject who receives the endoscopic examination, information such as a test result of a *Helicobacter pylori* test, a test result of a pepsinogen test, presence or absence of a *Helicobacter pylori* elimination treatment history, a test result of a CDH1 gene, presence or absence of an excision treatment history, a test result of an HER2 gene, a test result of an EB virus test, presence or absence of a dose of NSAIDs (non-steroidal anti-inflammatory drugs), and presence or absence of a subjective symptom of the subject.

In other words, according to the present embodiment, as the physical information of the subject who receives the endoscopic examination, at least one of information indicating a test result obtained by performing a test relating to a diagnosis target organ, information indicating a treatment history in the diagnosis target organ, information indicating a dose history of a drug relating to the diagnosis target organ, or information indicating presence or absence of a subjective symptom of the subject is inputted.

After inputting the physical information of the subject who receives the endoscopic examination, the user inserts the insertion section of the endoscope 11 into an inside of the subject and disposes the distal end portion of the insertion section in a position where an image of a desired object can be picked up inside the stomach of the subject.

When detecting that an instruction for completing the input of the physical information of the subject who receives the endoscopic examination is performed in the input I/F 123, the control unit 124 performs an operation for outputting the physical information to the diagnosis support apparatus 13.

When the main body apparatus 12 is turned on, the control unit 124 performs, on the light source unit 121, control for causing the light source unit 121 to sequentially or simultaneously generate the B light, the G light, and the R light as illumination light. According to such control by the control unit 124, the illumination light is supplied from the light source unit 121 to the endoscope 11. An image of return light from the subject illuminated by the illumination light is picked up in the image pickup unit 111. An endoscopic image EG corresponding to an image pickup signal outputted from the image pickup unit 111 to the main body apparatus 12 is generated in the image generating unit 122. The generated endoscopic image EG is sequentially outputted to the diagnosis support apparatus 13 frame by frame.

The abnormal-symptom identifying unit 13A performs, based on physical information outputted from the main body apparatus 12, identifying one abnormal symptom appearing in the stomach of the subject who receives the endoscopic examination. The abnormal-symptom identifying unit 13A outputs information indicating the one abnormal symptom identified by the processing explained above to the lesion-extraction-function control unit 13B.

Figure 3:
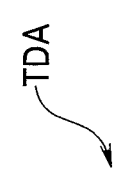
FIG. 3 is a diagram showing an example of table data used in processing of the diagnosis support apparatus according to the first embodiment.

More specifically, for example, the abnormal-symptom identifying unit 13A reads table data TDA shown in FIG. 3 from the storage medium 132 and collates the read table data TDA and the physical information outputted from the main body apparatus 12 to thereby identify one abnormal symptom appearing in the stomach of the subject who receives the endoscopic examination. FIG. 3 is a diagram showing an example of table data used in processing of the diagnosis support apparatus according to the first embodiment.

A "physical information" field of the table data TDA shown in FIG. 3 includes a plurality of items corresponding to the physical information outputted from the main body apparatus 12 (information inputted in the input I/F 123). In an "abnormal symptom" field of the table data TDA shown in FIG. 3 includes a plurality of items indicating symptoms of the stomach corresponding to respective items of the "physical information" field.

According to the table data TDA shown in FIG. 3, for example, when a test result indicating that a *Helicobacter pylori* test is positive is included in the physical information outputted from the main body apparatus 12 and a test result of a pepsinogen test is not included in the physical information, it is identified that the abnormal symptom appearing in the stomach of the subject who receives the endoscopic examination is bacterial infection.

According to the table data TDA shown in FIG. 3, for example, when a test result indicating that a *Helicobacter pylori* test is positive is included in the physical information outputted from the main body apparatus 12 and a test result indicating that a pepsinogen test is negative is included in the physical information, it is identified that the abnormal symptom appearing in the stomach of the subject who receives the endoscopic examination is an ulcer.

According to the table data TDA shown in FIG. 3, for example, when a test result indicating that a *Helicobacter pylori* test is positive is included in the physical information outputted from the main body apparatus 12 and a test result indicating that a pepsinogen test is positive is included in the physical information, it is identified that the abnormal symptom appearing in the stomach of the subject who receives the endoscopic examination is atrophic gastritis.

According to the table data TDA shown in FIG. 3, for example, when a test result indicating that a *Helicobacter pylori* test is negative is included in the physical information outputted from the main body apparatus 12 and a test result indicating that a pepsinogen test is positive is included in the physical information, it is identified that the abnormal symptom appearing in the stomach of the subject who receives the endoscopic examination is atrophic gastritis.

According to the table data TDA shown in FIG. 3, for example, when information indicating that *Helicobacter pylori* elimination treatment is completed is included in the physical information outputted from the main body apparatus 12, it is identified that the abnormal symptom appearing in the stomach of the subject who receives the endoscopic examination is elimination treatment completed.

According to the table data TDA shown in FIG. 3, for example, when a test result indicating that mutation is present in a CDH1 gene is included in the physical information outputted from the main body apparatus 12, it is identified that the abnormal symptom appearing in the stomach of the subject who receives the endoscopic examination is diffuse stomach cancer.

According to the table data TDA shown in FIG. 3, for example, when information indicating excision treatment completed is included and a test result indicating that mutation is present in an HER2 gene is included in the physical information outputted from the main body apparatus 12, it is identified that the abnormal symptom appearing in the stomach of the subject who receives the endoscopic examination is excision treatment completed.

According to the table data TDA shown in FIG. 3, for example, when a test result indicating that an EB virus test is positive is included in the physical information outputted from the main body apparatus 12, it is identified that the abnormal symptom appearing in the stomach of the subject who receives the endoscopic examination is atrophic gastritis.

According to the table data TDA shown in FIG. 3, for example, when information indicating that NSAIDs is being taken is included in the physical information outputted from the main body apparatus 12, it is identified that the abnormal symptom appearing in the stomach of the subject who receives the endoscopic examination is an ulcer.

According to the table data TDA shown in FIG. 3, for example, when information indicating that a subjective symptom of the subject is present is included in the physical information outputted from the main body apparatus 12, it is identified that the abnormal symptom appearing in the stomach of the subject who receives the endoscopic examination is an ulcer. Note that examples of the subjective symptom in such a case include a pain near a pit of a stomach, gastric hyperacidity, black stools, and anemia.

When one abnormal symptom appearing in the stomach of the subject who receives the endoscopic examination cannot be identified because, for example, an abnormal symptom corresponding to the physical information outputted from the main body apparatus 12 is not included in the table data TDA, the abnormal-symptom identifying unit 13A in the present embodiment outputs, to the lesion-extraction-function control unit 13B, information indicating that presence or absence of the abnormal symptom appearing in the stomach of the subject is unknown.

For example, when simultaneously identifying a plurality of abnormal symptoms corresponding to the table data TDA shown in FIG. 3, the abnormal-symptom identifying unit 13A in the present embodiment outputs, to the lesion-extraction-function control unit 13B, information indicating an abnormal symptom having the highest priority level among the plurality of abnormal symptoms. Note that priority levels of the respective abnormal symptoms included in the table data TDA shown in FIG. 3 are set in predetermined order corresponding to, for example, levels of risk values explained below.

The lesion-extraction-function control unit 13B performs, based on information outputted from the abnormal-symptom identifying unit 13A, processing for selecting one lesion extracting unit corresponding to one abnormal symptom included in the information out of the plurality of lesion extracting units included in the lesion extraction function unit 13C and performs control for causing the one lesion extracting unit to perform lesion extraction processing.

More specifically, for example, when information indicating that an abnormal symptom is bacterial infection is included in the information outputted from the abnormal-symptom identifying unit 13A, the lesion-extraction-function control unit 13B performs processing for selecting a lesion extracting unit LESA specialized for lesion extraction at a *Helicobacter pylori* infection time out of the plurality of lesion extracting units LES included in the lesion extraction function unit 13C and performs control for causing the lesion extracting unit LESA to perform the lesion extraction processing.

For example, when information indicating that the abnormal symptom is an ulcer is included in the information outputted from the abnormal-symptom identifying unit 13A, the lesion-extraction-function control unit 13B performs processing for selecting a lesion extracting unit LESB specialized for lesion extraction at an ulcer emergence time out of the plurality of lesion extracting units LES included in the lesion extraction function unit 13C and performs control for causing the lesion extracting unit LESB to perform the lesion extraction processing.

For example, when information indicating that the abnormal symptom is atrophic gastritis is included in the information outputted from the abnormal-symptom identifying unit 13A, the lesion-extraction-function control unit 13B performs processing for selecting a lesion extracting unit LESC specialized for lesion extraction at an atrophic gastritis emergence time out of the plurality of lesion extracting units LES included in the lesion extraction function unit 13C and performs control for causing the lesion extracting unit LESC to perform the lesion extraction processing.

For example, when information indicating that the abnormal symptom is elimination treatment completed is included in the information outputted from the abnormal-symptom identifying unit 13A, the lesion-extraction-function control unit 13B performs processing for selecting a lesion extracting unit LESD specialized for lesion extraction after *Helicobacter pylori* elimination out of the plurality of lesion extracting units LES included in the lesion extraction function unit 13C and performs control for causing the lesion extracting unit LESD to perform the lesion extraction processing.

For example, when information indicating that the abnormal symptom is diffuse stomach cancer is included in the information outputted from the abnormal-symptom identifying unit 13A, the lesion-extraction-function control unit 13B performs processing for selecting a lesion extracting unit LESE specialized for lesion extraction at a diffuse stomach cancer emergence time out of the plurality of lesion extracting units LES included in the lesion extraction function unit 13C and performs control for causing the lesion extracting unit LESE to perform the lesion extraction processing.

For example, when information indicating that the abnormal symptom is excision treatment completed is included in the information outputted from the abnormal-symptom identifying unit 13A, the lesion-extraction-function control unit 13B performs processing for selecting a lesion extracting unit LESF specialized for lesion extraction after stomach excision out of the plurality of lesion extracting units LES included in the lesion extraction function unit 13C and performs control for causing the lesion extracting unit LESF to perform the lesion extraction processing.

For example, when information indicating that presence or absence of an abnormal symptom is unknown is included in the information outputted from the abnormal-symptom identifying unit 13A (an abnormal symptom is not identified by the abnormal-symptom identifying unit 13A), the lesion-extraction-function control unit 13B performs processing for selecting a lesion extracting unit LESY for performing lesion extraction processing not specialized for a specific abnormal symptom that could appear in the stomach instead of selecting one lesion extracting unit LESX out of the plurality of lesion extracting units LES included in the lesion extraction function unit 13C and performs control for causing the lesion extracting unit LESY to perform the lesion extraction processing.

In other words, in the specific examples explained above, any one of the six lesion extracting units LESA, LESB, LESC, LESD, LESE, and LESF is equivalent to the lesion extracting unit LESX.

The lesion extraction function unit 13C performs, according to the control by the lesion-extraction-function control unit 13B, in the lesion extracting unit LESX or the lesion extracting unit LESY, lesion extraction processing for extracting a lesion candidate region LA from the endoscopic image EG outputted from the main body apparatus 12 and outputs, to the display control unit 13D, information capable of estimating a position of the lesion candidate region LA extracted by the lesion extraction processing to be identified.

Figure 4:
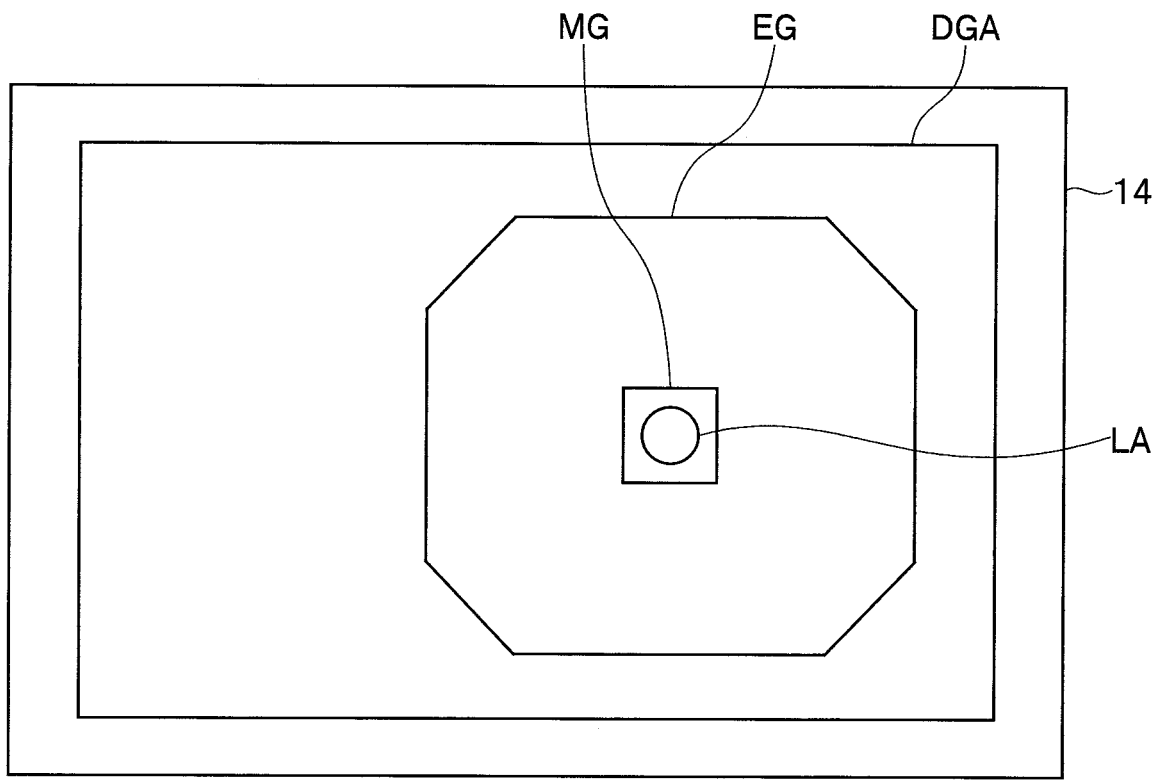
FIG. 4 is a diagram showing an example of a display image displayed according to the processing of the diagnosis support apparatus according to the first embodiment.

The display control unit 13D performs, based on the information outputted from the lesion extraction function unit 13C, processing for identifying a position of the lesion candidate region LA in the endoscopic image EG outputted from the main body apparatus 12 and generating a marker MG equivalent to a rectangular frame surrounding a periphery of the identified lesion candidate region LA. The display control unit 13D performs processing for generating a display image by adding the marker MG explained above to the endoscopic image EG and outputting the generated display image to the display apparatus 14. In other words, the display control unit 13D in the present embodiment performs processing for causing the display apparatus 14 to collectively display the endoscopic image EG obtained by picking up an image of the diagnosis target organ of the subject who receives the endoscopic examination and information indicating the position of the lesion candidate region LA extracted by the lesion extracting unit LESX or the lesion extracting unit LESY. With such processing of the display control unit 13D, for example, a display image DGA shown in FIG. 4 is displayed on the display apparatus 14. FIG. 4 is a diagram showing an example of a display image displayed according to processing of the diagnosis support apparatus according to the first embodiment.

Incidentally, for example, in processing for extracting a lesion candidate region from an endoscopic image obtained by picking up an image of an inside of a stomach, extraction accuracy of the lesion candidate region tends to change according to a state of a gastric mucosa of a subject who receives an endoscopic examination. More specifically, for example, in the gastric mucosa after *Helicobacter pylori* elimination treatment is performed, because, for example, a size of a lesion decreases and a color tone of the lesion is less conspicuous compared with the gastric mucosa before the elimination treatment is performed, the extraction accuracy in the processing for extracting the lesion candidate region from the endoscopic image tends to be lower than before the elimination treatment is performed.

In contrast, according to the present embodiment, physical information including one or more kinds of information capable of estimating a state of a stomach (a diagnosis target organ) of a subject who receives an endoscopic examination is inputted to the abnormal-symptom identifying unit 13A, one abnormal symptom corresponding to the physical information is identified by the abnormal-symptom identifying unit 13A, one lesion extracting unit most suitable for the one abnormal symptom is selected out of a plurality of lesion extracting units by the lesion-extraction-function control unit 13B, and processing for extracting a lesion candidate region from an endoscopic image in the one lesion extracting unit is performed by the lesion extraction function unit 13C. Therefore, according to the present embodiment, it is possible to secure extraction accuracy of a lesion in the diagnosis target organ.

Note that, according to the present embodiment, for example, the lesion-extraction-function control unit 13B may be configured to perform processing for setting sensitivity according to an instruction (an instruction of the user)

performed in the input I/F 123 and perform control for causing the lesion extracting unit LESX or the lesion extracting unit LESY to perform lesion extraction processing at the sensitivity. With such a configuration of the lesion-extraction-function control unit 13B explained above, for example, when the sensitivity of the lesion extraction processing performed in the lesion extracting unit LESX or the lesion extracting unit LESY is set to relatively high sensitivity, it is possible to relatively increase an extraction frequency of a lesion candidate region extracted from the endoscopic image EG. With the configuration of the lesion-extraction-function control unit 13B explained above, for example, when the sensitivity of the lesion extraction processing performed in the lesion extracting unit LESX or the lesion extracting unit LESY is set to relatively low sensitivity, it is possible to relatively increase probability of a lesion candidate region extracted from the endoscopic image EG (possibility that a lesion is actually included in the lesion candidate region). Note that, in the present embodiment, it is assumed that magnitude of the sensitivity of the lesion extraction processing is set as a value inversely proportional to magnitude of a threshold applied to parameters such as a pixel value acquired from the endoscopic image EG when a lesion candidate region included in the endoscopic image EG is detected.

According to the present embodiment, the lesion extraction processing in the lesion extracting unit LESX or the lesion extracting unit LESY is not limited to the lesion extraction processing performed on the endoscopic image obtained during the endoscopic examination (outputted from the main body apparatus 12) and may be lesion extraction processing performed on an endoscopic image obtained from a video of an endoscopic examination recorded in advance in, for example, a not-shown recording apparatus.

By modifying the configuration according to the present embodiment as appropriate, the configuration may be adapted to a case in which the diagnosis target organ of the subject who receives the endoscopic examination is an organ different from the stomach.

According to the present embodiment, as the physical information of the subject who receives the endoscopic examination, for example, information indicating at least one of a dietary habit of the subject, a smoking history of the subject, an age of the subject, sex of the subject, a race of the subject, or a family cancer history of the subject may be further included.

According to the present embodiment, when, for example, table data TDB shown in FIG. 5 is stored in the storage medium 132 instead of the table data TDA shown in FIG. 3, operations corresponding to the table data TDB may be performed in the respective units of the diagnosis support apparatus 13. Operations and the like according to such a modification of the present embodiment are explained below. Note that, in the following explanation, for simplification, specific explanation concerning portions to which the operations and the like explained above are applicable is omitted as appropriate. FIG. 5 is a diagram showing an example of table data used in processing of a diagnosis support apparatus according to a modification of the embodiment.

The abnormal-symptom identifying unit 13A performs, based on the physical information outputted from the main body apparatus 12, processing for respectively identifying one abnormal symptom appearing in the stomach of the subject who receives the endoscopic examination, a level of a lesion risk in the one abnormal symptom, and propriety of recommendation of a special light observation for the one abnormal symptom. The abnormal-symptom identifying unit 13A outputs, to the lesion-extraction-function control unit 13B, information correlating the one abnormal symptom identified by the processing explained above, the level of the lesion risk identified by the processing explained above, and the propriety of the recommendation of the special light observation for the one abnormal symptom identified by the processing explained above.

More specifically, for example, the abnormal-symptom identifying unit 13A reads the table data TDB shown in FIG. 5 from the storage medium 132 and collates the read table data TDB and the physical information outputted from the main body apparatus 12 to thereby respectively identify one abnormal symptom appearing in the stomach of the subject who receives the endoscopic examination, a risk value set in advance according to the one abnormal symptom, and propriety of recommendation of the special light observation for the one abnormal symptom.

A "physical information" field of the table data TDB shown in FIG. 5 includes a plurality of items corresponding to the physical information outputted from the main body apparatus 12 (the information inputted in the input I/F 123). An "abnormal symptom" field of the table data TDB shown in FIG. 5 includes a plurality of items indicating symptoms of the stomach corresponding to the respective items of the "physical information" field. A "lesion risk" field of the table data TDB shown in FIG. 5 includes a plurality of items indicating risk values equivalent to values set according to levels of occurrence frequencies of lesions of each of the symptoms of the stomach in the "abnormal symptom" field. A "special light observation" field of the table data TDB shown in FIG. 5 includes a plurality of items indicating propriety of recommendation of a special light observation (a narrow-band light observation) for the respective symptoms of the stomach in the "abnormal symptom" field. Note that it is assumed that values of the respective items in the "lesion risk" field of the table data TDB shown in FIG. 5 are set as relative values larger than 0 and smaller than 100.

According to the table data TDB shown in FIG. 5, for example, when a test result indicating that a *Helicobacter pylori* test is positive is included in the physical information outputted from the main body apparatus 12 and a test result of a pepsinogen test is not included in the physical information, it is identified that the abnormal symptom appearing in the stomach of the subject who receives the endoscopic examination is bacterial infection, a risk value corresponding to the abnormal symptom is 10, and switching to the special light observation is not recommended for the abnormal symptom.

According to the table data TDB shown in FIG. 5, for example, when a test result indicating that a *Helicobacter pylori* test is positive is included in the physical information outputted from the main body apparatus 12 and a test result indicating that a pepsinogen test is negative is included in the physical information, it is identified that the abnormal symptom appearing in the stomach of the subject who receives the endoscopic examination is an ulcer, a risk value corresponding to the abnormal symptom is 5, and switching to the special light observation is not recommended for the abnormal symptom.

According to the table data TDB shown in FIG. 5, for example, when a test result indicating that a *Helicobacter pylori* test is positive is included in the physical information outputted from the main body apparatus 12 and a test result indicating that a pepsinogen test is positive is included in the physical information, it is identified that the abnormal symptom appearing in the stomach of the subject who receives the endoscopic examination is atrophic gastritis, a risk value corresponding to the abnormal symptom is 20, and switching to the special light observation is not recommended for the abnormal symptom.

According to the table data TDB shown in FIG. 5, for example, when a test result indicating that a *Helicobacter pylori* test is negative is included in the physical information outputted from the main body apparatus 12 and a test result indicating that a pepsinogen test is positive is included in the physical information, it is identified that the abnormal symptom appearing in the stomach of the subject who receives the endoscopic examination is atrophic gastritis, a risk value corresponding to the abnormal symptom is 30, and switching to the special light observation is not recommended for the abnormal symptom.

According to the table data TDB shown in FIG. 5, for example, when information indicating that *Helicobacter pylori* elimination treatment is completed is included in the physical information outputted from the main body apparatus 12, it is identified that the abnormal symptom appearing in the stomach of the subject who receives the endoscopic examination is elimination treatment completed, a risk value corresponding to the abnormal symptom is 50, and switching to the special light observation is recommended for the abnormal symptom.

According to the table data TDB shown in FIG. 5, for example, when a test result indicating that mutation is present in a CDH1 gene is included in the physical information outputted from the main body apparatus 12, it is identified that the abnormal symptom appearing in the stomach of the subject who receives the endoscopic examination is diffuse stomach cancer, a risk value corresponding to the abnormal symptom is 50, and switching to the special light observation is recommended for the abnormal symptom.

According to the table data TDB shown in FIG. 5, for example, when information indicating excision treatment completed is included in the physical information outputted from the main body apparatus 12 and a test result indicating that mutation is present in an HER2 gene is included in the physical information, it is identified that the abnormal symptom appearing in the stomach of the subject who receives the endoscopic examination is excision treatment completed, a risk value corresponding to the abnormal symptom is 50, and switching to the special light observation is not recommended for the abnormal symptom.

According to the table data TDB shown in FIG. 5, for example, when a test result indicating that an EB virus test is positive is included in the physical information outputted from the main body apparatus 12, it is identified that the abnormal symptom appearing in the stomach of the subject who receives the endoscopic examination is atrophic gastritis, a risk value corresponding to the abnormal symptom is 10, and switching to the special light observation is not recommended for the abnormal symptom.

According to the table data TDB shown in FIG. 5, for example, when information indicating that NSAIDs is being taken is included in the physical information outputted from the main body apparatus 12, it is identified that the abnormal symptom appearing in the stomach of the subject who receives the endoscopic examination is an ulcer, a risk value corresponding to the abnormal symptom is 5, and switching to the special light observation is not recommended for the abnormal symptom.

According to the table data TDB shown in FIG. 5, for example, when information indicating that a subjective symptom of the subject is present is included in the physical information outputted from the main body apparatus 12, it is identified that the abnormal symptom appearing in the stomach of the subject who receives the endoscopic examination is an ulcer, a risk value corresponding to the abnormal symptom is 5, and switching to the special light observation is not recommended for the abnormal symptom.

When failing in identifying one abnormal symptom appearing in the stomach of the subject who receives the endoscopic examination because, for example, an abnormal symptom corresponding to the physical information outputted from the main body apparatus 12 is not included in the table data TDB, the abnormal-symptom identifying unit 13A in the modification outputs, to the lesion-extraction-function control unit 13B, information indicating that presence or absence of the abnormal symptom appearing in the stomach of the subject is unknown.

When failing in identifying, from the table data TDB, one abnormal symptom appearing in the stomach of the subject who receives the endoscopic examination, the abnormal-symptom identifying unit 13A in the modification outputs, to the lesion-extraction-function control unit 13B, information indicating a risk value and propriety of recommendation of the special light observation set according to information included in the physical information outputted from the main body apparatus 12. More specifically, for example, when information indicating that finding is present in an X-ray image of the stomach is included in the physical information outputted from the main body apparatus 12, the abnormal-symptom identifying unit 13A in the modification outputs, to the lesion-extraction-function control unit 13B, information indicating that switching to the special light observation is not recommended.

Note that, for example, when information indicating a request about, for example, whether the subject actively requests for detection of a lesion is included in the physical information outputted from the main body apparatus 12, the abnormal-symptom identifying unit 13A in the modification may increase or decrease, according to the information, a risk value acquired from the table data TDB.

More specifically, for example, when information indicating that the subject actively requests for detection of a lesion is included in the physical information outputted from the main body apparatus 12, the abnormal-symptom identifying unit 13A in the modification may increase, according to the information, the risk value acquired from the table data TDB. For example, when information indicating that the subject does not actively requests for detection of a lesion is included in the physical information outputted from the main body apparatus 12, the abnormal-symptom identifying unit 13A in the modification may decrease, according to the information, the risk value acquired from the table data TDB.

For example, when simultaneously identifying a plurality of abnormal symptoms corresponding to the table data TDB shown in FIG. 5, the abnormal-symptom identifying unit 13A in the modification outputs, to the lesion-extraction-function control unit 13B, information correlating one abnormal symptom having the highest priority level among the plurality of abnormal symptoms, a risk value corresponding to the one abnormal symptom, and propriety of recommendation of the special light observation for the one abnormal symptom. Note that priority levels of the respective abnormal symptoms included in the table data TDB shown in FIG. 5 only have to be set in predetermined order corresponding to, for example, levels of risk values included in the "lesion risk" field.

Based on the information outputted from the abnormal-symptom identifying unit 13A, the lesion-extraction-function control unit 13B in this modification performs processing for selecting one lesion extracting unit corresponding to the one abnormal symptom included in the information out of the plurality of lesion extracting units included in the lesion extraction function unit 13C, performs processing for setting sensitivity corresponding to the risk value (a level of a lesion risk) included in the information, and performs control for causing the one lesion extracting unit to perform the lesion extraction processing at the sensitivity. The lesion-extraction-function control unit 13B in this modification performs, on the lesion extraction function unit 13C, control for causing the lesion extraction function unit 13C to output, in correlation with each other, a processing result of the lesion extraction processing in the one lesion extracting unit selected as explained above and information indicating the propriety of the recommendation of the special light observation included in the information outputted from the abnormal-symptom identifying unit 13A.

More specifically, for example, when information indicating that the abnormal symptom is bacterial infection and information indicating that the risk value is 10 are included in the information outputted from the abnormal-symptom identifying unit 13A, the lesion-extraction-function control unit 13B performs processing for selecting the lesion extracting unit LESA out of the plurality of lesion extracting units LES included in the lesion extraction function unit 13C, performs processing for setting the sensitivity corresponding to the risk value to SP, and performs control for causing the lesion extracting unit LESA to perform the lesion extraction processing at the sensitivity SP.

For example, when information indicating that the abnormal symptom is an ulcer and information indicating that the risk value is 5 are included in the information outputted from the abnormal-symptom identifying unit 13A, the lesion-extraction-function control unit 13B performs processing for selecting the lesion extracting unit LESB out of the plurality of lesion extracting units LES included in the lesion extraction function unit 13C, performs processing for setting the sensitivity corresponding to the risk value to SP, and performs control for causing the lesion extracting unit LESB to perform the lesion extraction processing at the sensitivity SP.

For example, when information indicating that the abnormal symptom is strophic gastritis and information indicating that the risk value is a value of 20 or 30 are included in the information outputted from the abnormal-symptom identifying unit 13A, the lesion-extraction-function control unit 13B performs processing for selecting the lesion extracting unit LESC out of the plurality of lesion extracting units LES included in the lesion extraction function unit 13C, performs processing for setting the sensitivity corresponding to the risk value to SQ (>SP), and performs control for causing the lesion extracting unit LESC to perform the lesion extraction processing at the sensitivity SQ.

For example, when information indicating that the abnormal symptom is atrophic gastritis and information indicating that the risk value is 10 are included in the information outputted from the abnormal-symptom identifying unit 13A, the lesion-extraction-function control unit 13B performs processing for selecting the lesion extracting unit LESC out of the plurality of lesion extracting units LES included in the lesion extraction function unit 13C, performs processing for setting the sensitivity corresponding to the risk value to SP, and performs control for causing the lesion extracting unit LESC to perform the lesion extraction processing at the sensitivity SP.

For example, when information indicating that the abnormal symptom is elimination treatment completed and information indicating that the risk value is 50 are included in the information outputted from the abnormal-symptom identifying unit 13A, the lesion-extraction-function control unit 13B performs processing for selecting the lesion extracting unit LESD out of the plurality of lesion extracting units LES included in the lesion extraction function unit 13C, performs processing for setting the sensitivity corresponding to the risk value to SR (>SQ) and performs control for causing the lesion extracting unit LESD to perform the lesion extraction processing at the sensitivity SR.

For example, when information indicating that the abnormal symptom is diffuse stomach cancer and information indicating that the risk value is 50 are included in the information outputted from the abnormal-symptom identifying unit 13A, the lesion-extraction-function control unit 13B performs processing for selecting the lesion extracting unit LESE out of the plurality of lesion extracting units LES included in the lesion extraction function unit 13C, performs processing for setting the sensitivity corresponding to the risk value to SR, and performs control for causing the lesion extracting unit LESE to perform the lesion extraction processing at the sensitivity SR.

For example, when information indicating that the abnormal symptom is excision treatment completed and information indicating that the risk value is 50 are included in the information outputted from the abnormal-symptom identifying unit 13A, the lesion-extraction-function control unit 13B performs processing for selecting the lesion extracting unit LESF out of the plurality of lesion extracting units LES included in the lesion extraction function unit 13C, performs processing for setting the sensitivity corresponding to the risk value to SR, and performs control for causing the lesion extracting unit LESF to perform the lesion extraction processing at the sensitivity SR.

For example, when information indicating that presence or absence of the abnormal symptom is unknown and information indicating that the risk value is 80 are included in the information outputted from the abnormal-symptom identifying unit 13A, the lesion-extraction-function control unit 13B performs processing for selecting the lesion extracting unit LESY included in the lesion extraction function unit 13C, performs processing for setting the sensitivity corresponding to the risk value to SR, and performs control for causing the lesion extracting unit LESY to perform the lesion extraction processing at the sensitivity SR.

For example, when information indicating that presence or absence of the abnormal symptom is unknown and information indicating that the risk value is 10 are included in the information outputted from the abnormal-symptom identifying unit 13A, the lesion-extraction-function control unit 13B performs processing for selecting the lesion extracting unit LESY included in the lesion extraction function unit 13C, performs processing for setting the sensitivity corresponding to the risk value to SP, and performs control for causing the lesion extracting unit LESY to perform the lesion extraction processing at the sensitivity SP.

The lesion extraction function unit 13C performs, according to the control by the lesion-extraction-function control unit 13B, in the lesion extracting unit LESX or the lesion extracting unit LESY, lesion extraction processing for extracting the lesion candidate region LA from the endoscopic image EG outputted from the main body apparatus 12 and collectively outputs, to the display control unit 13D, information capable of estimating a position of the lesion candidate region LA extracted by the lesion extraction processing to be identified and information indicating the propriety of the recommendation of the special light observation identified by the abnormal-symptom identifying unit 13A.

The display control unit 13D performs, based on the information outputted from the lesion extraction function unit 13C, processing for identifying a position of the lesion candidate region LA in the endoscopic image EG outputted from the main body apparatus 12 and generating the marker MG equivalent to a rectangular frame surrounding a periphery of the identified lesion candidate region LA.

When information indicating that switching to the special light observation is not recommended is included in the information outputted from the lesion extraction function unit 13C, the display control unit 13D performs processing for generating the same display image as the display image DGA illustrated in FIG. 4 and outputting the display image to the display apparatus 14.

Figure 6:
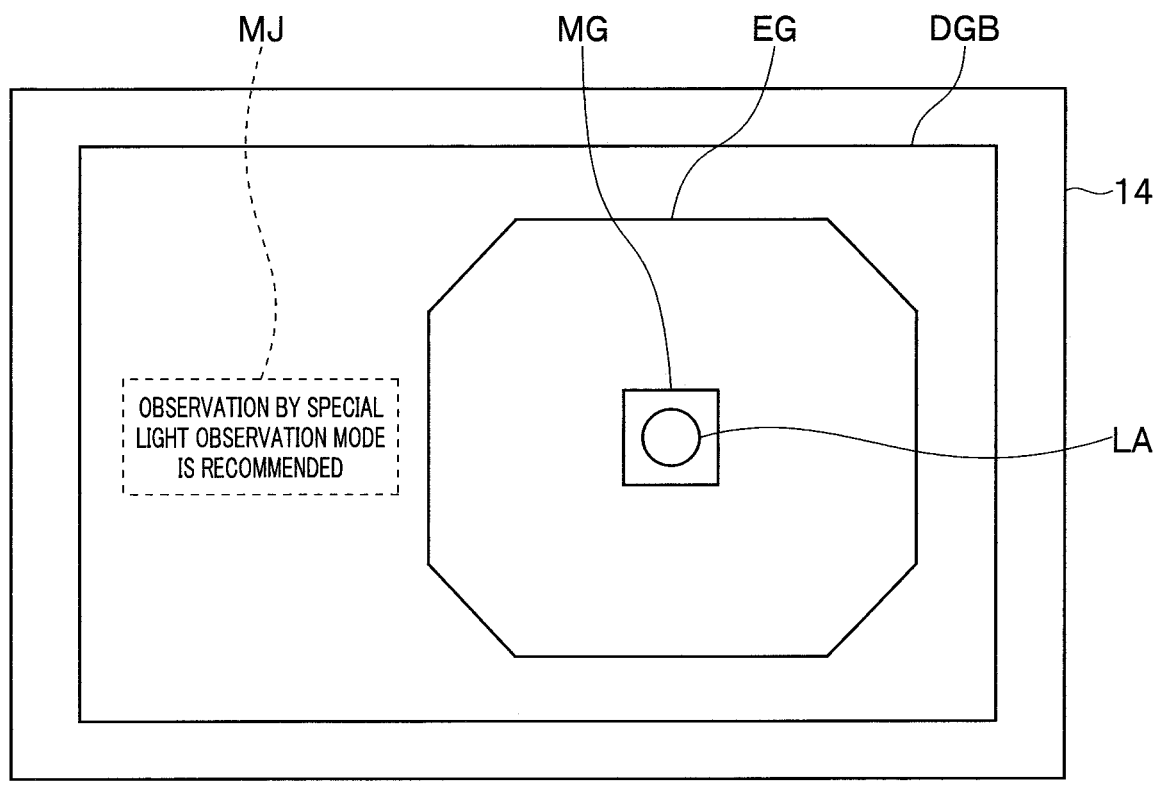
FIG. 6 is a diagram showing an example of a display image displayed according to the processing of the diagnosis support apparatus according to the modification of the first embodiment.

When information indicating that switching to the special light observation is recommended is included in the information outputted from the lesion extraction function unit 13C, the display control unit 13D performs processing for generating character information MJ including a character string for urging switching from the white light observation mode to the special light observation mode. When information indicating that switching to the special light observation is recommended is included in the information outputted from the lesion extraction function unit 13C, the display control unit 13D performs processing for adding the marker MG explained above to the endoscopic image EG, generating a display image by adding the character information MJ explained above to a display region on an outside of the endoscopic image EG, and outputting the generated display image to the display apparatus 14. In other words, when detecting that switching to the special light observation is recommended for the one abnormal symptom identified by the abnormal-symptom identifying unit 13A, the display control unit 13D in the modification performs processing for causing the display apparatus 14 to collectively display the endoscopic image EG obtained by picking up an image of the diagnosis target organ of the subject who receives the endoscopic examination, information indicating the position of the lesion candidate region LA extracted by the lesion extracting unit LESX or the lesion extracting unit LESY, and information for urging implementation of the special light observation. According to such processing of the display control unit 13D, for example, a display image DGB shown in FIG. 6 is displayed on the display apparatus 14. FIG. 6 is a diagram showing an example of a display image displayed according to processing of the diagnosis support apparatus according to the modification of the first embodiment.

Note that, according to the modification, instead of causing the display apparatus 14 to display the character information MJ, for example, voice corresponding to the character information MJ may be outputted from a not-shown speaker.

According to the modification, for example, the respective lesion extracting units included in the lesion extraction function unit 13C may be configured to perform lesion extraction processing further including processing for calculating likelihood LK of the lesion candidate region LA extracted from the endoscopic image EG and collectively output, to the display control unit 13D, information indicating a position of the lesion candidate region LA, information indicating a calculation result of the likelihood LK, and information indicating the propriety of the recommendation of the special light observation identified by the abnormal-symptom identifying unit 13A. Further, in such a configuration, for example, when information indicating that switching to the special light observation is recommended is included in the information outputted from the lesion extraction function unit 13C and the likelihood LK indicated by the information outputted from the lesion extraction function unit 13C belongs to a predetermined range, an operation for generating the character information MJ and causing the display apparatus 14 to display the character information MJ may be performed by the display control unit 13D.

According to the modification, for example, at least one lesion extracting unit among the plurality of lesion extracting units included in the lesion extraction function unit 13C may be subdivided according to sensitivity in the lesion extraction processing. More specifically, for example, instead of the lesion extracting unit LESA, a lesion extracting unit LESAP that performs, at the sensitivity SP, lesion extraction processing specialized for lesion extraction at a *Helicobacter pylori* infection time, a lesion extracting unit LESAQ that performs the lesion extraction processing at the sensitivity SQ, and a lesion extracting unit LESAR that performs the lesion extraction processing at the sensitivity SR may be provided in the lesion extraction function unit 13C.

As explained above, according to the modification, it is possible to select one lesion extracting unit out of the plurality of lesion extracting units included in the lesion extraction function unit 13C using substantially the same method as the method in the embodiment explained above (the method using the table data TDA). Further, according to the modification, it is possible to perform the lesion extraction processing in the one lesion extracting unit selected as explained above at sensitivity set according to an occurrence frequency of a lesion in the diagnosis target organ of the subject who receives the endoscopic examination. Accordingly, according to the modification, it is possible to secure extraction accuracy of the lesion in the diagnosis target organ.

Note that, according to the modification, for example, when information indicating that the diagnosis target organ of the subject who receives the endoscopic examination is an esophagus and a race of the subject is a Western is included in the physical information outputted from the main body apparatus 12, processing for identifying whether Barrett esophagus appears in the diagnosis target organ may be performed by the abnormal-symptom identifying unit 13A. Further, according to the modification, when it is identified that one abnormal symptom appearing in the esophagus of the subject who receives the endoscopic examination is the Barrett esophagus, processing for selecting one lesion extracting unit corresponding to the one abnormal symptom, processing for setting sensitivity corresponding to the one abnormal symptom, and control for causing the one lesion extracting unit to perform the lesion extraction processing at the sensitivity may be performed in the lesion-extraction-function control unit 13B.

Second Embodiment

Figure 7:
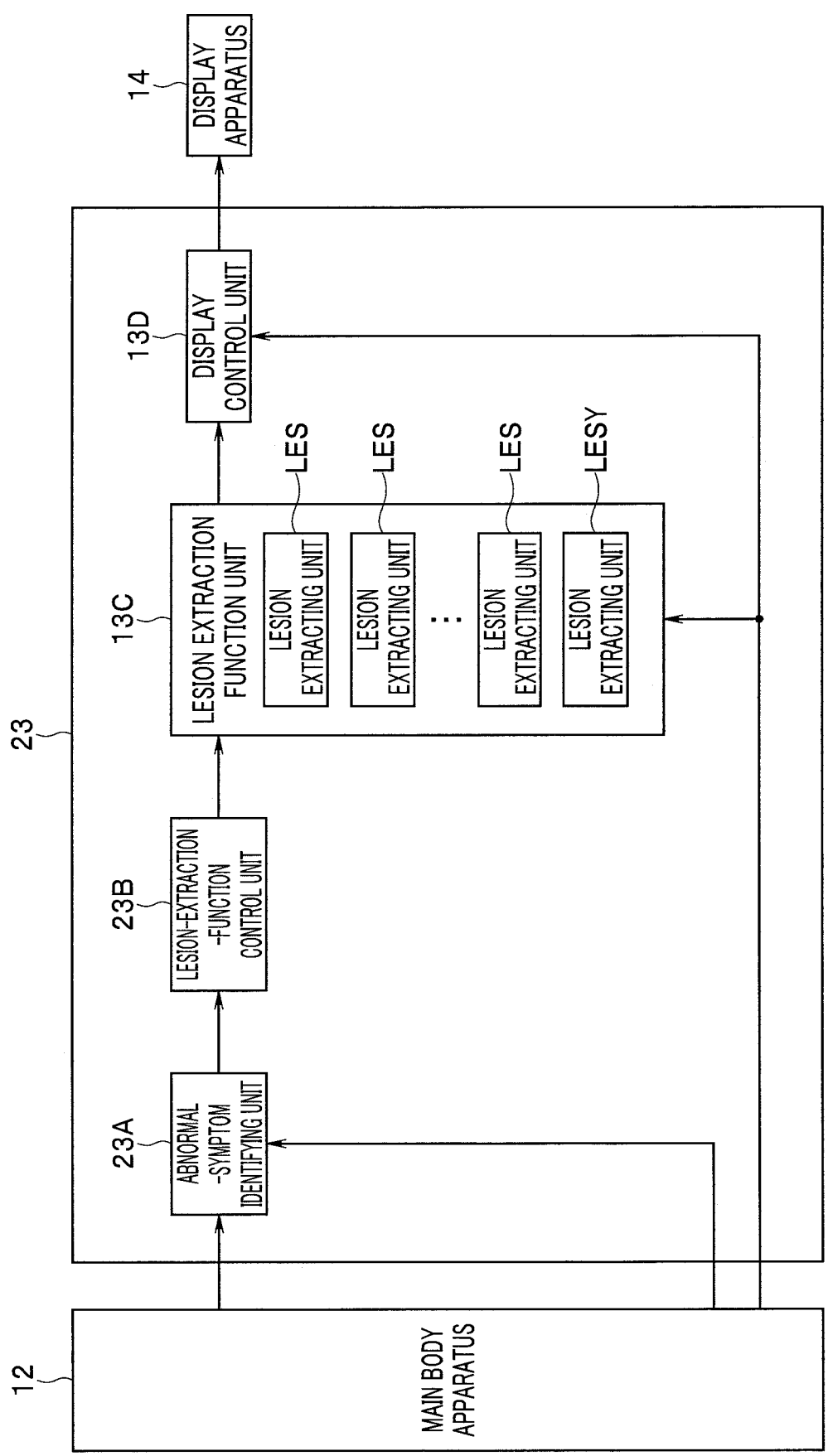
FIG. 7 is a block diagram for explaining a specific example of a configuration of a diagnosis support apparatus according to a second embodiment.
Figure 8:
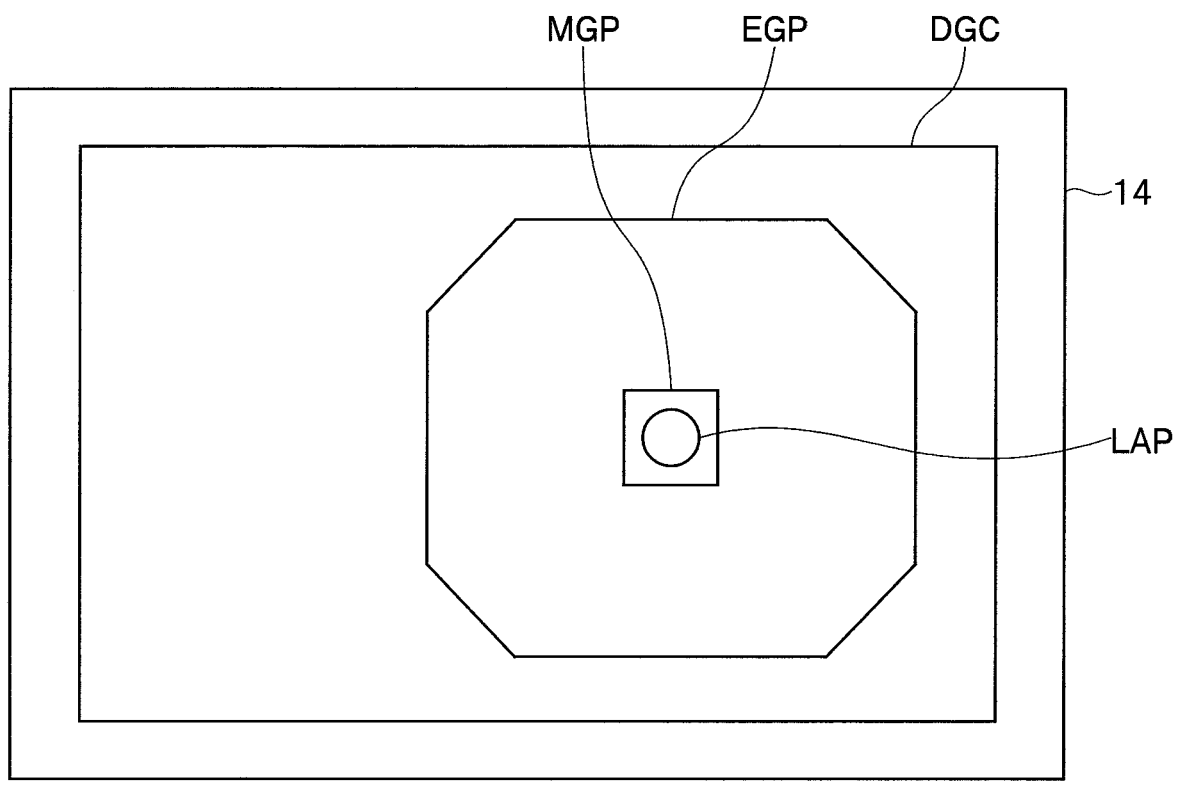
FIG. 8 is a diagram showing an example of a display image displayed according to processing of the diagnosis support apparatus according to the second embodiment.

FIG. 7 and FIG. 8 relate to a second embodiment.

Note that, in the present embodiment, detailed explanation concerning portions having the same components and the like as the components and the like in the first embodiment is omitted as appropriate and portions having components and the like different from the components and the like in the first embodiment are mainly explained.

The endoscope system 1 in the present embodiment includes, for example, a diagnosis support apparatus 23 shown in FIG. 7 instead of the diagnosis support apparatus 13. FIG. 7 is a block diagram for explaining a specific example of a configuration of a diagnosis support apparatus according to the second embodiment.

The diagnosis support apparatus 23 has substantially the same configuration as a diagnosis support apparatus in which the abnormal-symptom identifying unit 13A of the diagnosis support apparatus 13 is replaced with an abnormal-symptom identifying unit 23A and the lesion-extraction-function control unit 13B of the diagnosis support apparatus 13 is replaced with a lesion-extraction-function control unit 23B.

The abnormal-symptom identifying unit 23A is configured to, when detecting an abnormal finding detection instruction outputted from the main body apparatus 12, perform, based on an endoscopic image inputted at timing when the abnormal finding detection instruction is detected, processing for identifying one abnormal symptom appearing in a diagnosis target organ of a subject who receives an endoscopic examination. The abnormal-symptom identifying unit 23A is configured to output information indicating the one abnormal symptom identified as explained above to the lesion-extraction-function control unit 23B. In other words, the abnormal-symptom identifying unit 23A is configured to perform, based on an endoscopic image obtained by picking up an image of the diagnosis target organ of the subject who receives the endoscopic examination, processing for identifying one abnormal symptom appearing in the diagnosis target organ.

More specifically, the abnormal-symptom identifying unit 23A performs processing for identifying one abnormal symptom using, for example, a feature value (at least one of a hue, a chroma, or brightness) representing a color tone of an endoscopic image outputted from the main body apparatus 12 and a statistical amount (at least one of dispersion of pixel values and distribution of luminance gradients) calculated based on pixel values of a plurality of pixels included in a region of interest set in the endoscopic image.

Alternatively, for example, when the abnormal-symptom identifying unit 23A includes a classifier configured to be able to recognize, with machine learning using an image obtained by picking up an image of an inside of a predetermined organ, a plurality of abnormal symptoms that could appear in the predetermined organ and classify the plurality of abnormal symptoms for each of the abnormal symptoms, the abnormal-symptom identifying unit 23A performs processing for identifying one abnormal symptom based on an output result obtained by inputting, to the classifier, a pixel value and the like of the endoscopic image outputted from the main body apparatus 12.

The abnormal-symptom identifying unit 23A is configured to, in a period from timing when one abnormal finding detection instruction outputted from the main body apparatus 12 to timing when a next abnormal finding detection instruction outputted from the main body apparatus 12, continue to output information indicating one abnormal symptom identified according to the one abnormal finding detection instruction to the lesion-extraction-function control unit 23B.

The lesion-extraction-function control unit 23B is configured to perform, based on the information outputted from the abnormal-symptom identifying unit 23A, processing for selecting one lesion extracting unit corresponding to the one abnormal symptom included in the information out of the plurality of lesion extracting units included in the lesion extraction function unit 13C and perform control for causing the one lesion extracting unit to perform the lesion extraction processing.

Subsequently, action in the present embodiment is explained.

After connecting the respective units of the endoscope system 1 and turning on the endoscope system 1, a user inserts the insertion section of the endoscope 11 into an inside of a subject and disposes the distal end portion of the insertion section in a position where an image of a desired object inside a stomach of the subject can be picked up. For example, at time TP belonging to a period in which the desired object inside the stomach of the subject is observed, the user operates the abnormal finding detection instruction switch of the input I/F 123 to thereby perform an abnormal finding detection instruction.

When the main body apparatus 12 is turned on, the control unit 124 performs, on the light source unit 121, control for causing the light source unit 121 to sequentially or simultaneously generating B light, G light, and R light as illumination light. According to such control by the control unit 124, the illumination light is supplied from the light source unit 121 to the endoscope 11, an image of return light from an object illuminated by the illumination light is picked up in the image pickup unit 111, the endoscopic image EG corresponding to an image pickup signal outputted from the image pickup unit 111 to the main body apparatus 12 is generated in the image generating unit 122, and the generated endoscopic image EG is sequentially outputted to the diagnosis support apparatus 23 frame by frame.

When detecting that the abnormal finding detection instruction is performed in the input I/F 123, the control unit 124 performs an operation for outputting the abnormal finding detection instruction to the diagnosis support apparatus 23.

When detecting, at the time TP, the abnormal finding detection instruction outputted from the main body apparatus 12, the abnormal-symptom identifying unit 23A performs, based on the endoscopic image EG inputted from the main body apparatus 12 at the time TP, processing for identifying one abnormal symptom appearing in the diagnosis target organ of the subject who receives the endoscopic examination. The abnormal-symptom identifying unit 23A outputs information indicating the one abnormal symptom identified by the processing explained above to the lesion-extraction-function control unit 23B.

More specifically, for example, when detecting that a color tone of the endoscopic image EG outputted from the main body apparatus 12 is a high-chroma red color tone (a color tone equivalent to a reddened mucous membrane), the abnormal-symptom identifying unit 23A specifies that an abnormal symptom appearing in the stomach of the subject who receives the endoscopic examination is bacterial infection.

For example, when detecting that the color tone of the endoscopic image EG outputted from the main body apparatus 12 is a low-chroma red color tone (a color tone equivalent to a discolored mucous membrane), the abnormal-symptom identifying unit 23A specifies that the abnormal symptom appearing in the stomach of the subject who receives the endoscopic examination is bacterial infection.

For example, when detecting that the color tone of the endoscopic image EG outputted from the main body apparatus 12 is a white color tone (a color tone caused by clouded mucus), the abnormal-symptom identifying unit 23A specifies that the abnormal symptom appearing in the stomach of the subject who receives the endoscopic examination is bacterial infection.

For example, when detecting that a black fur or a white fur is present in the endoscopic image EG by applying processing using, for example, the method disclosed in Japanese Patent Application Laid-Open Publication No. 2015-181594 to the endoscopic image EG outputted from the main body apparatus 12, the abnormal-symptom identifying unit 23A specifies that the abnormal symptom appearing in the stomach of the subject who receives the endoscopic examination is an ulcer.

For example, when detecting that an arborizing vessel is present in the endoscopic image EG by applying predetermined processing to the endoscopic image EG outputted from the main body apparatus 12, the abnormal-symptom identifying unit 23A specifies that the abnormal symptom appearing in the stomach of the subject who receives the endoscopic examination is atrophic gastritis.

In other words, with the operation and the like of the abnormal-symptom identifying unit 23A explained above, one abnormal symptom appearing in the diagnosis target organ of the subject who receives the endoscopic examination is identified based on the endoscopic image EGP outputted from the main body apparatus 12 at a point in time of the time TP and information indicating the identified one abnormal symptom is outputted to the lesion-extraction-function control unit 23B.

For example, when failing in identifying one abnormal symptom from the endoscopic image EG outputted from the main body apparatus 12, the abnormal-symptom identifying unit 23A outputs, to the lesion-extraction-function control unit 23B, information indicating that presence or absence of the abnormal symptom appearing in the stomach of the subject is unknown.

In a period from the time TP when one abnormal finding detection instruction outputted from the main body apparatus 12 is detected to time TQ when a next abnormal finding detection instruction outputted from the main body apparatus 12 is detected, the abnormal-symptom identifying unit 23A continues to output, to the lesion-extraction-function control unit 23B, information indicating one abnormal symptom identified according to the one abnormal finding detection instruction.

Based on the information outputted from the abnormal-symptom identifying unit 23A, the lesion-extraction-function control unit 23B performs processing for selecting one lesion extracting unit corresponding to the one abnormal symptom included in the information out of the plurality of lesion extracting units included in the lesion extraction function unit 13C and performs control for causing the one lesion extracting unit to perform the lesion extraction processing.

More specifically, for example, when information indicating that the abnormal symptom is bacterial infection is included in the information outputted from the abnormal-symptom identifying unit 23A, the lesion-extraction-function control unit 23B performs processing for selecting the lesion extracting unit LESA out of the plurality of lesion extracting units LES included in the lesion extraction function unit 13C and performs control for causing the lesion extracting unit LESA to perform the lesion extraction processing.

For example, when information indicating that the abnormal symptom is an ulcer is included in the information outputted from the abnormal-symptom identifying unit 23A, the lesion-extraction-function control unit 23B performs processing for selecting the lesion extracting unit LESB out of the plurality of lesion extracting units LES included in the lesion extraction function unit 13C and performs control for causing the lesion extracting unit LESB to perform the lesion extraction processing.

For example, when information indicating that the abnormal symptom is atrophic gastritis is included in the information outputted from the abnormal-symptom identifying unit 23A, the lesion-extraction-function control unit 23B performs processing for selecting the lesion extracting unit LESC out of the plurality of lesion extracting units LES included in the lesion extraction function unit 13C and performs control for causing the lesion extracting unit LESC to perform the lesion extraction processing.

For example, when information indicating that presence or absence of the abnormal symptom is unknown (w % ben the abnormal symptom is not identified by the abnormal-symptom identifying unit 23A) is included in the information outputted from the abnormal-symptom identifying unit 23A, the lesion-extraction-function control unit 23B performs processing for selecting the lesion extracting unit LESY included in the lesion extraction function unit 13C and performs control for causing the lesion extracting unit LESY to perform the lesion extraction processing.

In other words, in the specific examples explained above, any one of the three lesion extracting units LESA, LESB, and LESC is equivalent to the lesion extracting unit LESX.

The lesion extraction function unit 13C performs, according to the control by the lesion-extraction-function control unit 23B, in the lesion extracting unit LESX or the lesion extracting unit LESY, lesion extraction processing for extracting the lesion candidate region LAP from the endoscopic image EGP outputted from the main body apparatus 12 and outputs, to the display control unit 13D, information capable of estimating a position of the lesion candidate region LAP extracted by the lesion extraction processing to be identified.

The display control unit 13D performs, based on the information outputted from the lesion extraction function unit 13C, processing for identifying a position of the lesion candidate region LAP in the endoscopic image EGP inputted at a point in time of the time TP and generating a marker MGP equivalent to a rectangular frame surrounding a periphery of the identified lesion candidate region LAP. The display control unit 13D performs processing for generating a display image by adding the marker MGP explained above to the endoscopic image EGP and outputting the generated display image to the display apparatus 14. In other words, the display control unit 13D in the present embodiment performs processing for causing the display apparatus 14 to collectively display the endoscopic image EGP obtained by picking up an image of the diagnosis target organ of the subject who receives the endoscopic examination and information indicating the position of the lesion candidate region LAP extracted by the lesion extracting unit LESX or the lesion extracting unit LESY. With such processing of the display control unit 13D, for example, a display image DGC shown in FIG. 8 is displayed on the display apparatus 14. FIG. 8 is a diagram showing an example of a display image displayed according to processing of the diagnosis support apparatus according to the second embodiment.

As explained above, according to the present embodiment, an endoscopic image obtained by picking up an image of an inside of a stomach (a diagnosis target organ) of the subject who receives the endoscopic examination is inputted to the abnormal-symptom identifying unit 23A, one abnormal symptom corresponding to a processing result of processing for the endoscopic image is identified by the abnormal-symptom identifying unit 23A, one lesion extracting unit most suitable for the one abnormal symptom is selected out of a plurality of lesion extracting units by the lesion-extraction-function control unit 23B, and processing for extracting a lesion candidate region from the endoscope image in the one lesion extracting unit is performed by the lesion extraction function unit 13C. Accordingly, according to the present embodiment, it is possible to secure extraction accuracy of a lesion in the diagnosis target organ.

As explained above, according to the present embodiment, at every timing when the abnormal finding detection instruction is performed in the input I/F 123, processing for identifying, based on the endoscopic image, one abnormal symptom appearing in the stomach of the subject is performed by the abnormal-symptom identifying unit 23A. Accordingly, according to the present embodiment, for example, in a situation in which the user is observing a desired observation target site inside the stomach such as a cardia, a fundus, a gastric body, and a pylorus, by operating the abnormal finding detection instruction switch of the input IF 123 at appropriate timing, the user can accurately extract a lesion corresponding to an abnormal symptom appearing in the desired observation target site.

Note that, according to the present embodiment, for example, when the diagnosis target organ of the subject who receives the endoscopic examination is a stomach, processing for identifying one abnormal symptom other than bacterial infection, an ulcer, and atrophic gastritis may be performed in the abnormal-symptom identifying unit 23A and processing for selecting one lesion extracting unit corresponding to the one abnormal symptom and control for causing the one lesion extracting unit to perform the lesion extraction processing may be performed in the lesion-extraction-function control unit 23B.

According to the present embodiment, for example, when the diagnosis target organ of the subject who receives the endoscopic examination is an esophagus, it may be identified by the abnormal-symptom identifying unit 23A, based on the endoscopic image EG outputted from the main body apparatus 12, that one abnormal symptom appearing in the diagnosis target organ is Barret esophagus and processing for selecting one lesion extracting unit corresponding to the one abnormal symptom and control for causing the one lesion extracting unit to perform the lesion extraction processing may be performed in the lesion-extraction-function control unit 23B.

Third Embodiment

Figure 9:
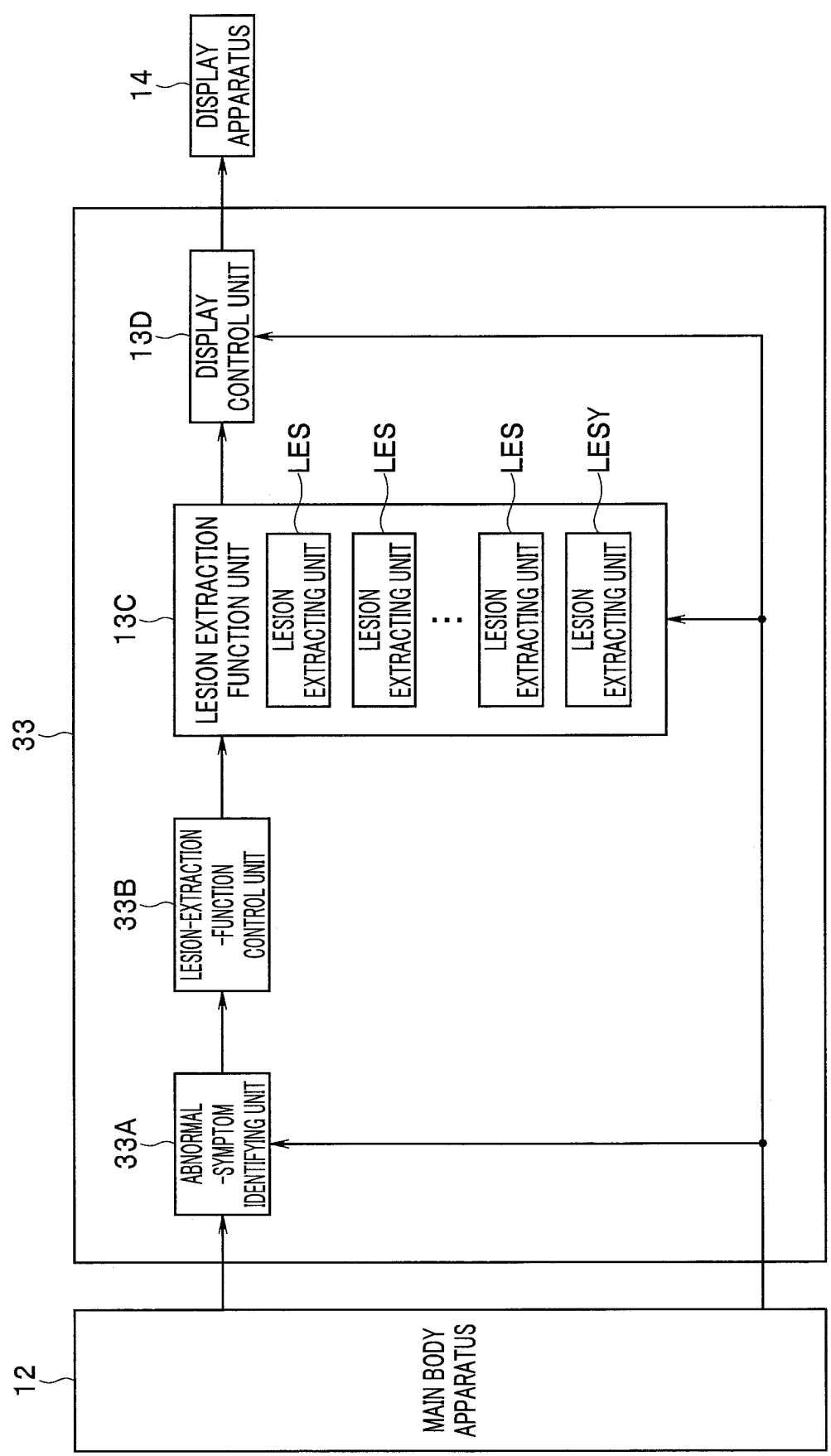
FIG. 9 is a block diagram for explaining a specific example of a configuration of a diagnosis support apparatus according to a third embodiment.
Figure 10:
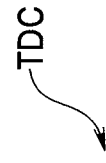
FIG. 10 is a diagram showing an example of table data used in processing of the diagnosis support apparatus according to the third embodiment.

FIG. 9 and FIG. 10 relate to a third embodiment.

Note that, in the present embodiment, detailed explanation concerning portions having the same components and the like as the components and the like in at least one of the first and second embodiments is omitted as appropriate. Portions having components and the like different from the components and the like in both of the first and second embodiments are mainly explained.

The endoscope system 1 in the present embodiment includes, for example, a diagnosis support apparatus 33 shown in FIG. 9 instead of the diagnosis support apparatus 13. FIG. 9 is a block diagram for explaining a specific example of a configuration of a diagnosis support apparatus according to the third embodiment.

The diagnosis support apparatus 33 has substantially the same configuration as a diagnosis support apparatus in which the abnormal-symptom identifying unit 13A of the diagnosis support apparatus 13 is replaced with an abnormal-symptom identifying unit 33A and the lesion-extraction-function control unit 13B of the diagnosis support apparatus 13 is replaced with a lesion-extraction-function control unit 33B.

The abnormal-symptom identifying unit 33A is configured to perform, based on physical information outputted from the main body apparatus 12, processing for identifying one abnormal symptom appearing in a diagnosis target organ of a subject who receives an endoscopic examination.

The abnormal-symptom identifying unit 33A is configured to perform processing for identifying an observation target site equivalent to an anatomical site of the diagnosis target organ included in an endoscopic image outputted from the main body apparatus 12. In other words, the observation target site explained above is identified as one site among a plurality of sites in a case in which the diagnosis target organ is anatomically classified.

More specifically, for example, when the abnormal-symptom identifying unit 33A includes a classifier configured to be able to recognize, with machine learning using an image obtained by picking up an image of a plurality of sites on an inside of a predetermined organ, the plurality of sites and classify the plurality of sites for each of the sites, the abnormal-symptom identifying unit 33A performs processing for identifying an observation target site based on an output result obtained by inputting, to the classifier, a pixel value and the like of the endoscopic image outputted from the main body apparatus 12.

Note that, according to the present embodiment, for example, when an angle knob (not shown) capable of performing operation for changing an angle of the distal end portion of the insertion section of the endoscope 11 is provided in the operation section of the endoscope 11, processing for identifying an observation target site may be performed by the abnormal-symptom identifying unit 33A using a detection result obtained by detecting an operation state of the angle knob.

The abnormal-symptom identifying unit 33A is configured to perform, based on the one abnormal symptom and the observation target site identified by the processing explained above, processing for respectively identifying a level of a lesion risk corresponding to the one abnormal symptom appearing in the observation target site and propriety of recommendation of a special light observation for the one abnormal symptom appearing in the observation target site. The abnormal-symptom identifying unit 33A is configured to output, to the lesion-extraction-function control unit 33B, information correlating the one abnormal symptom identified by the processing explained above, the level of the lesion risk identified by the processing explained above, and the propriety of the recommendation of the special light observation identified by the processing explained above.

The lesion-extraction-function control unit 33B is configured to, based on the information outputted from the abnormal-symptom identifying unit 33A, perform processing for selecting one lesion extracting unit corresponding to the one abnormal symptom included in the information out of the plurality of lesion extracting units included in the lesion extraction function unit 13C, perform processing for setting sensitivity corresponding to the level of the lesion risk included in the information, and perform control for causing the one lesion extracting unit to perform the lesion extraction processing at the sensitivity. The lesion-extraction-function control unit 33B is configured to perform, on the lesion extraction function unit 13C, control for causing the lesion extraction function unit 13C to output, in correlation with each other, a processing result of the lesion extraction processing in the one lesion extracting unit selected as explained above and information indicating the propriety of recommendation of the special light observation included in the information outputted from the abnormal-symptom identifying unit 33A.

Subsequently, action in the present embodiment is explained.

After connecting the respective units of the endoscope system 1 and turning on the endoscope system 1, a user inserts the insertion section of the endoscope 11 into an inside of a subject and disposes the distal end portion of the insertion section in a position where an image of a desired object inside a stomach of the subject can be picked up.

When the main body apparatus 12 is turned on, the control unit 124 performs, on the light source unit 121, control for causing the light source unit 121 to sequentially or simultaneously generate the B light, the G light, and the R light as illumination light. According to such control by the control unit 124, the illumination light is supplied from the light source unit 121 to the endoscope 11. An image of return light from a subject illuminated by the illumination light is picked up in the image pickup unit 111. The endoscopic image EG corresponding to an image pickup signal outputted from the image pickup unit 111 to the main body apparatus 12 is generated in the image generating unit 122. The generated endoscopic image EG is sequentially outputted to the diagnosis support apparatus 33 frame by frame.

The abnormal-symptom identifying unit 33A performs, based on physical information outputted from the main body apparatus 12, processing for identifying one abnormal symptom appearing in a stomach of a subject who receives an endoscopic examination.

More specifically, for example, the abnormal-symptom identifying unit 33A reads the table data TDA shown in FIG. 3 from the storage medium 132 and collates the read table data TDA and the physical information outputted from the main body apparatus 12 to thereby identify one abnormal symptom appearing in the stomach of the subject who receives the endoscopic examination.

The abnormal-symptom identifying unit 33A performs, based on an endoscopic image outputted from the main body apparatus 12, processing for identifying an observation target site in the stomach of the subject who receives the endoscopic examination.

More specifically, the abnormal-symptom identifying unit 33A specifies, for example, based on the endoscopic image outputted from the main body apparatus 12, to which of a gastric body, an antral zone, a fornix, a gastric angle, and another site the observation target site in the stomach belongs.

The abnormal-symptom identifying unit 33A performs, based on the one abnormal symptom and the observation target site identified by the processing explained above, processing for respectively identifying a level of a lesion risk corresponding to the one abnormal symptom appearing in the observation target site and propriety of recommendation of a special light observation for the one abnormal symptom appearing in the observation target site. The abnormal-symptom identifying unit 33A outputs, to the lesion-extraction-function control unit 33B, information correlating the one abnormal symptom identified by the processing explained above, the level of the lesion risk identified by the processing explained above, and the propriety of the recommendation of the special light observation identified by the processing explained above.

More specifically, for example, the abnormal-symptom identifying unit 33A reads a table data TDC shown in FIG. 10 from the storage medium 132 and collates the read table data TDC and the one abnormal symptom and the observation target site identified by the processing explained above to thereby respectively identify a level of a lesion risk corresponding to the one abnormal symptom appearing in the observation target site and propriety of the recommendation of the special light observation for the one abnormal symptom appearing in the observation target site. FIG. 10 is a diagram showing an example of a table data used in processing of the diagnosis support apparatus according to the third embodiment.

An "abnormal symptom" field of the table data TDC shown in FIG. 10 includes a plurality of items obtained by subdividing, according to sites of the stomach, at least one symptom among symptoms of the stomach included in the "abnormal symptom" field of the table data TDA shown in FIG. 3. A "detailed site" field of the table data TDC shown in FIG. 10 includes a plurality of items indicating sites of the stomach corresponding to the respective items of the "abnormal symptom" field. A "lesion risk" field of the table data TDC shown in FIG. 10 includes a plurality of items indicating risk values equivalent to values set according to levels of occurrence frequencies of lesions for each of combinations of the symptoms of the stomach in the "abnormal symptom" field and the sites of the stomach in the "detailed site" field. A "special light observation" field of the table data TDC shown in FIG. 10 includes a plurality of items indicating necessity of a special light observation (a narrow-band light observation) for the symptoms of the stomach in the "abnormal symptom" field in the sites of the stomach in the "detailed site" field. Note that it is assumed that values of the respective items in the "lesion risk" field of the table data TDC shown in FIG. 10 are set as relative values larger than 0 and smaller than 100.

According to the table data TDC shown in FIG. 10, for example, when it is identified that an abnormal symptom appearing in a stomach of a subject who receives an endoscopic examination is atrophic gastritis and it is identified that an observation target site in the stomach is a gastric body or an antral zone, it is respectively identified that a risk value corresponding to the abnormal symptom appearing in the observation target site is 25 and switching to the special light observation is not recommended for the abnormal symptom appearing in the observation target site.

According to the table data TDC shown in FIG. 10, for example, when it is identified that an abnormal symptom appearing in a stomach of a subject who receives an endoscopic examination is atrophic gastritis and it is identified that an observation target site in the stomach is a fomix, it is respectively identified that a risk value corresponding to the abnormal symptom appearing in the observation target site is 8 and switching to the special light observation is not recommended for the abnormal symptom appearing in the observation target site.

According to the table data TDC shown in FIG. 10, for example, when it is identified that an abnormal symptom appearing in a stomach of a subject who receives an endoscopic examination is atrophic gastritis and it is identified that an observation target site in the stomach is another site corresponding to none of a gastric body, an antral zone, and a fomix, it is respectively identified that a risk value corresponding to the abnormal symptom appearing in the observation target site is 20 and switching to the special light observation is not recommended for the abnormal symptom appearing in the observation target site.

According to the table data TDC shown in FIG. 10, for example, when it is identified that an abnormal symptom appearing in a stomach of a subject who receives an endoscopic examination is an ulcer and it is identified that an observation target site in the stomach is a gastric angle or a gastric body, it is respectively identified that a risk value corresponding to the abnormal symptom appearing in the observation target site is 10 and switching to the special light observation is not recommended for the abnormal symptom appearing in the observation target site.

According to the table data TDC shown in FIG. 10, for example, when it is identified that an abnormal symptom appearing in a stomach of a subject who receives an endoscopic examination is an ulcer and it is identified that an observation target site in the stomach is another site corresponding to none of a gastric angle and a gastric body, it is respectively identified that a risk value corresponding to the abnormal symptom appearing in the observation target site is 5 and switching to the special light observation is not recommended for the abnormal symptom appearing in the observation target site.

According to the table data TDC shown in FIG. 10, for example, when it is identified that an abnormal symptom appearing in a stomach of a subject who receives an endoscopic examination is diffuse stomach cancer and it is identified that an observation target site in the stomach is a gastric angle, it is respectively identified that a risk value corresponding to the abnormal symptom appearing in the observation target site is 50 and switching to the special light observation is recommended for the abnormal symptom appearing in the observation target site.

According to the table data TDC shown in FIG. 10, for example, when it is identified that an abnormal symptom appearing in a stomach of a subject who receives an endoscopic examination is diffuse stomach cancer and it is identified that an observation target site in the stomach is a gastric body, it is respectively identified that a risk value corresponding to the abnormal symptom appearing in the observation target site is 40 and switching to the special light observation is recommended for the abnormal symptom appearing in the observation target site.

According to the table data TDC shown in FIG. 10, for example, when it is identified that an abnormal symptom appearing in a stomach of a subject who receives an endoscopic examination is diffuse stomach cancer and it is identified that an observation target site in the stomach is a fomix, it is respectively identified that a risk value corresponding to the abnormal symptom appearing in the observation target site is 20 and switching to the special light observation is not recommended for the abnormal symptom appearing in the observation target site.

According to the table data TDC shown in FIG. 10, for example, when it is identified that an abnormal symptom appearing in a stomach of a subject who receives an endoscopic examination is diffuse stomach cancer and it is identified that an observation target site in the stomach is another site corresponding to none of a gastric angle, a gastric body, and a fomix, it is respectively identified that a risk value corresponding to the abnormal symptom appearing in the observation target site is 35 and switching to the special light observation is recommended for the abnormal symptom appearing in the observation target site.

In other words, according to the operation and the like of the abnormal-symptom identifying unit 33A explained above, based on the physical information outputted from the main body apparatus 12 and an endoscopic image EGQ outputted from the main body apparatus 12, one abnormal symptom appearing in the diagnosis target organ of the subject who receives the endoscopic examination, a level of a lesion risk corresponding to the one abnormal symptom appearing in an observation target site in the diagnosis target organ, and propriety of recommendation of the special light observation for the one abnormal symptom appearing in the observation target site are respectively identified.

When failing in identifying one abnormal symptom appearing in the stomach of the subject who receives the endoscopic examination because, for example, an abnormal symptom corresponding to the physical information outputted from the main body apparatus 12 is not included in the table data TDA, the abnormal-symptom identifying unit 33A outputs, to the lesion-extraction-function control unit 33B, information indicating that presence or absence of the abnormal symptom appearing in the stomach of the subject is unknown.

Based on the information outputted from the abnormal-symptom identifying unit 33A, the lesion-extraction-function control unit 33B performs processing for selecting one lesion extracting unit corresponding to the one abnormal symptom included in the information out of the plurality of lesion extracting units included in the lesion extraction function unit 13C, performs processing for setting sensitivity corresponding to the risk value (a level of a lesion risk) included in the information, and performs control for causing the one lesion extracting unit to perform the lesion extraction processing at the sensitivity. The lesion-extraction-function control unit 33B in the modification performs, on the lesion extraction function unit 13C, control for causing the lesion extraction function unit 13C to output, in correlation with each other, a processing result of the lesion extraction processing in the one lesion extracting unit selected as explained above and information indicating the propriety of the recommendation of the special light observation included in the information outputted from the abnormal-symptom identifying unit 33A.

More specifically, for example, when information indicating that the abnormal symptom is atrophic gastritis and information indicating that the risk value is 20 or 25 are included in the information outputted from the abnormal-symptom identifying unit 33A, the lesion-extraction-function control unit 33B performs processing for selecting the lesion extracting unit LESC out of the plurality of lesion extracting units LES included in the lesion extraction function unit 13C, performs processing for setting the sensitivity corresponding to the risk value to SM, and performs control for causing the lesion extracting unit LESC to perform the lesion extraction processing at the sensitivity SM.

For example, when information indicating that the abnormal symptom is atrophic gastritis and information indicating that the risk value is 8 are included in the information outputted from the abnormal-symptom identifying unit 33A, the lesion-extraction-function control unit 33B performs processing for selecting the lesion extracting unit LESC out of the plurality of lesion extracting units LES included in the lesion extraction function unit 13C, performs processing for setting the sensitivity corresponding to the risk value to SK (<SM), and performs control for causing the lesion extracting unit LESC to perform the lesion extraction processing at the sensitivity SK.

For example, when information indicating that the abnormal symptom is an ulcer and information indicating that the risk value is 10 are included in the information outputted from the abnormal-symptom identifying unit 33A, the lesion-extraction-function control unit 33B performs processing for selecting the lesion extracting unit LESB out of the plurality of lesion extracting units LES included in the lesion extraction function unit 13C, performs processing for setting the sensitivity corresponding to the risk value to SL (SK<SL<SM), and performs control for causing the lesion extracting unit LESB to perform the lesion extraction processing at the sensitivity SL.

For example, when information indicating that the abnormal symptom is an ulcer and information indicating that the risk value is 5 are included in the information outputted from the abnormal-symptom identifying unit 33A, the lesion-extraction-function control unit 33B performs processing for selecting the lesion extracting unit LESB out of the plurality of lesion extracting units LES included in the lesion extraction function unit 13C, performs processing for setting the sensitivity corresponding to the risk value to SK, and performs control for causing the lesion extracting unit LESB to perform the lesion extraction processing at the sensitivity SK.

For example, when information indicating that the abnormal symptom is diffuse stomach cancer and information indicating that the risk value is any one value of 35, 40, or 50 are included in the information outputted from the abnormal-symptom identifying unit 33A, the lesion-extraction-function control unit 33B performs processing for selecting the lesion extracting unit LESE out of the plurality of lesion extracting units LES included in the lesion extraction function unit 13C, performs processing for setting the sensitivity corresponding to the risk value to SN (>SM), and performs control for causing the lesion extracting unit LESE to perform the lesion extraction processing at the sensitivity SN.

For example, when information indicating that the abnormal symptom is diffuse stomach cancer and information indicating that the risk value is 20 are included in the information outputted from the abnormal-symptom identifying unit 33A, the lesion-extraction-function control unit 33B performs processing for selecting the lesion extracting unit LESE out of the plurality of lesion extracting units LES included in the lesion extraction function unit 13C, performs processing for setting the sensitivity corresponding to the risk value to SM, and performs control for causing the lesion extracting unit LESE to perform the lesion extraction processing at the sensitivity SM.

For example, when information indicating that presence or absence of the abnormal symptom is unknown (the abnormal symptom is not identified by the abnormal-symptom identifying unit 33A) is included in the information outputted from the abnormal-symptom identifying unit 33A, the lesion-extraction-function control unit 33B performs processing for selecting the lesion extracting unit LESY included in the lesion extraction function unit 13C, performs processing for setting the sensitivity corresponding to the risk value to one sensitivity equivalent to a default value among the sensitivities SK. SL, SM, and SN and performs control for causing the lesion extracting unit LESY to perform the lesion extraction processing at the one sensitivity.

In other words, in the specific examples explained above, any one of the three lesion extracting units LESB, LESC, and LESE is equivalent to the lesion extracting unit LESX.

The lesion extraction function unit 13C performs, according to the control by the lesion-extraction-function control unit 33B, in the lesion extracting unit LESX or the lesion extracting unit LESY, lesion extraction processing for extracting the lesion candidate region LA from the endoscopic image EG outputted from the main body apparatus 12 and outputs, to the display control unit 13D, information capable of identifying a position of the lesion candidate region LA extracted by the lesion extraction processing to be identified.

The display control unit 13D performs, based on the information outputted from the lesion extraction function unit 13C, processing for identifying a position of the lesion candidate region LA in the endoscopic image EG outputted from the main body apparatus 12 and generating the marker MG equivalent to a rectangular frame surrounding a periphery of the identified lesion candidate region LA. The display control unit 13D performs processing for generating a display image by adding the marker MG explained above to the endoscopic image EG and outputting the generated display image to the display apparatus 14. With such processing of the display control unit 13D, the same display image as the display image DGA illustrated in FIG. 4 is displayed on the display apparatus 14.

As explained above, according to the present embodiment, it is possible to select one lesion extracting unit out of the plurality of lesion extracting units included in the lesion extraction function unit 13C using substantially the same method as the method explained in the first embodiment (the method using the table data TDA). Further, according to the present embodiment, it is possible to perform the lesion extraction processing in the one lesion extracting unit selected as explained above at sensitivity set according to an occurrence frequency of a lesion in the observation target site in the diagnosis target organ of the subject who receives the endoscopic examination. Accordingly, according to the present embodiment, it is possible to secure extraction accuracy of the lesion in the diagnosis target organ. According to the present embodiment, for example, it is possible to surely preform extraction of a lesion candidate region in a case in which a site having a relatively high occurrence frequency of a predetermined lesion in the diagnosis target organ of the subject who receives the endoscopic examination is observed. It is possible to suppress extraction of a lesion candidate region in a case in which a site having a relatively low occurrence frequency of the predetermined lesion is observed.

Note that, the abnormal-symptom identifying unit 33A in the present embodiment may identify, by applying, for example, the same processing as the processing explained in the second embodiment to the endoscopic image EG outputted from the main body apparatus 12, which of an ulcer and atrophic gastritis the abnormal symptom appearing in the stomach of the subject who receives the endoscopic examination is. The abnormal-symptom identifying unit 33A in the present embodiment may identify, by applying, for example, processing disclosed in Japanese Patent No. 5242381 to the endoscopic image EG outputted from the main body apparatus 12, that the abnormal symptom appearing in the stomach of the subject who receives the endoscopic examination is diffuse stomach cancer.

The present invention is not limited to the embodiments explained above. It goes without saying that various changes and applications are possible within a range not departing from the gist of the invention.

What is claimed is:

1. A control apparatus comprising:
one or more processors comprising hardware, wherein the one or more processors are configured to:
identify, based on physical information inputted, an estimated state of a diagnosis target organ;

select a lesion extraction process associated with the estimated state of the diagnosis target organ from a plurality of different lesion extraction processes for extracting a lesion candidate region from an endoscopic image; and perform the lesion extraction process selected to extract the lesion candidate region from the endoscope image.

2. The control apparatus according to claim 1, wherein the one or more processors are configured to identify propriety of recommendation of a special light observation for the estimated state of the diagnosis target organ.

3. The control apparatus according to claim 2, wherein the one or more processors are configured to cause a display apparatus to collectively display the endoscopic image, information indicating a position of the lesion candidate region extracted, and information for urging implementation of the special light observation.

4. The control apparatus according to claim 1, wherein the processor is further configured to identify an observation target site equivalent to an anatomical site of the diagnosis target organ included in the endoscopic image and identify a level of a lesion risk corresponding to the one abnormal symptom appearing in the observation target site.

5. The control apparatus according to claim 4, wherein the processor is further configured to perform processing for setting sensitivity corresponding to the level of the lesion risk and causing the control apparatus to perform extraction of the lesion candidate region at the sensitivity.

6. The control apparatus according to claim 1, wherein the one or more processors are configured to cause a display apparatus to collectively display the endoscopic image and information indicating a position of the lesion candidate region extracted.

7. A diagnosis support method comprising:
identifying, based on physical information inputted, an estimated state of a diagnosis target organ of a subject;
selecting a lesion extraction process associated with the estimated state of the diagnosis target organ from a plurality of different lesion extraction processes for extracting a lesion candidate region from an endoscopic image; and
performing the lesion extraction process selected to extract the lesion candidate region from the endoscope image.

8. The diagnosis support method according to claim 7, wherein the physical information comprises at least one of:
information indicating a test result obtained by performing a test relating to the diagnosis target organ;
information indicating a treatment history in the diagnosis target organ, information indicating a dose history of a drug relating to the diagnosis target organ; and
information indicating presence or absence of a subjective symptom of the subject.

9. The diagnosis support method according to claim 7, further comprising:
identifying a level of a lesion risk in in the estimated state of the diagnosis target organ.

10. The diagnosis support method according to claim 9, further comprising:
setting sensitivity corresponding to the identified level of the lesion risk; and
performing the lesion extraction process at the sensitivity set.

11. The diagnosis support method according to claim 7, further comprising:
identifying propriety of recommendation of a special light observation for the estimated state of the diagnosis target organ.

12. The diagnosis support method according to claim 11, further comprising:
controlling a display apparatus to collectively display the endoscopic image, information indicating a position of the lesion candidate region extracted, and information for urging implementation of the special light observation.

13. The diagnosis support method according to claim 7, further comprising:
identifying an observation target site equivalent to an anatomical site of the diagnosis target organ included in the endoscopic image; and
identifying a level of a lesion risk corresponding to the estimated state of the diagnosis target organ appearing in the observation target site.

14. The diagnosis support method according to claim 13, further comprising:
setting sensitivity corresponding to the level of the lesion risk; and
performing extraction of the lesion candidate region at the sensitivity.

15. The diagnosis support method according to claim 7, further comprising:
controlling a display apparatus to collectively display the endoscopic image and information indicating a position of the lesion candidate region extracted.

16. The diagnosis support method according to claim 7, further comprising:
setting sensitivity according to an instruction of a user; and
performing the lesion extraction process at the sensitivity.

17. The diagnosis support method according to claim 7, further comprising:
identifying propriety of recommendation of a special light observation for the estimated state of the diagnosis target organ.

18. A computer-readable non-transitory recording medium recording a program, the program, when executed, cause one or more computers to execute:
identifying, based on physical information inputted, an estimated state of a diagnosis target organ;
selecting a lesion extraction process associated with the estimated state of the diagnosis target organ from a plurality of different lesion extraction processes for extracting a lesion candidate region from an endoscopic image; and
performing the lesion extraction process selected to extract the lesion candidate region from the endoscope image.

19. The computer-readable non-transitory recording medium according to claim 18, wherein the program, when executed, causes the one or more computers to execute:
identify propriety of recommendation of a special light observation for the estimated state of the diagnosis target organ.

20. The computer-readable non-transitory recording medium according to claim 19, wherein the program, when executed, causes the one or more computers to execute:
control a display to collectively display the endoscopic image, information indicating a position of the lesion candidate region, and information for urging implementation of the special light observation.

* * * * *